United States Patent
Rodriguez Cutillas et al.

(10) Patent No.: US 9,110,076 B2
(45) Date of Patent: Aug. 18, 2015

(54) METHOD FOR QUANTIFYING MODIFIED PEPTIDES

(75) Inventors: Pedro Rodriguez Cutillas, London (GB); Bart Vanhaesebroeck, London (GB)

(73) Assignee: HVIVO SERVICES LIMITED, London (GB)

( * ) Notice: Subject to any disclaimer, the term of this patent is extended or adjusted under 35 U.S.C. 154(b) by 0 days.

(21) Appl. No.: 13/259,271

(22) PCT Filed: Apr. 16, 2010

(86) PCT No.: PCT/GB2010/000770
§ 371 (c)(1),
(2), (4) Date: Dec. 6, 2011

(87) PCT Pub. No.: WO2010/119261
PCT Pub. Date: Oct. 21, 2010

(65) Prior Publication Data
US 2012/0070844 A1   Mar. 22, 2012

(30) Foreign Application Priority Data
Apr. 17, 2009   (GB) ................................. 0906698.6

(51) Int. Cl.
*C12Q 1/37*   (2006.01)
*G01N 33/68*   (2006.01)

(52) U.S. Cl.
CPC ........ *G01N 33/6848* (2013.01); *G01N 33/6842* (2013.01)

(58) Field of Classification Search
None
See application file for complete search history.

(56) References Cited

U.S. PATENT DOCUMENTS

| | | | |
|---|---|---|---|
| 6,818,454 | B2 | 11/2004 | Goshe et al. |
| 2003/0153007 | A1 | 8/2003 | Chen et al. |
| 2005/0164324 | A1 | 7/2005 | Gygi |
| 2006/0148093 | A1 | 7/2006 | Gygi et al. |
| 2008/0221802 | A1 | 9/2008 | Oda et al. |

FOREIGN PATENT DOCUMENTS

| | | |
|---|---|---|
| WO | 03/102220 A3 | 12/2003 |
| WO | 2005/106923 A3 | 11/2005 |
| WO | 2007/127767 A2 | 11/2007 |
| WO | 2007/144606 A2 | 12/2007 |
| WO | 2010/006333 A2 | 1/2010 |

OTHER PUBLICATIONS

Frewen et al., (Anal. Chem. 2006; vol. 78, pp. 5678-5684).*
Thringholm et al., (Proteomics 2009;vol. 9, 1451-1468).*
Alcolea, M. P., et al., Increased confidence in large-scale phosphoproteomics data by complementary mass spectrometric techniques and matching of phosphopeptide data sets, J Proteome Res. Aug. 2009;8(8):3808-15.
Barglow, K. T., et al., Activity-based protein profiling for the functional annotation of enzymes, Nat Methods. Oct. 2007;4(10):822-7.
Blethrow, J. D., et al, Covalent capture of kinase-specific phosphopeptides reveals Cdk1-cyclin B substrates, Proc Natl Acad Sci U S A. Feb. 5, 2008;105(5):1442-7.
Cutillas, P. R., et al., Quantification of gel-separated proteins and their phosphorylation sites by LC-MS using unlabeled internal standards: analysis of phosphoprotein dynamics in a B cell lymphoma cell line, Mol Cell Proteomics. Aug. 2005;4(8):1038-51.
Cutillas, P. R., et al., Ultrasensitive and absolute quantification of the phosphoinositide 3-kinase/Akt signal transduction pathway by mass spectrometry, Proc Natl Acad Sci U S A. Jun. 13, 2006;103(24):8959-64.
Cutillas, P. R., et al., Quantitative profile of five murine core proteomes using label-free functional proteomics, Mol Cell Proteomics. Sep. 2007;6(9):1560-73.
Ficarro, S. B., et al., Automated immobilized metal affinity chromatography/nano-liquid chromatography/electrospray ionization mass spectrometry platform for profiling protein phosphorylation sites, Rapid Commun Mass Spectrom. 2005;19(1):57-71.
Gerber, S. A., et al., Absolute quantification of proteins and phosphoproteins from cell lysates by tandem MS, Proc Natl Acad Sci U S A. Jun. 10, 2003;100(12):6940-5.
Gygi, S. P., et al., Quantitative analysis of complex protein mixtures using isotope-coded affinity tags, Nat Biotechnol. Oct. 1999;17(10):994-9.
Hummel, J., et al, ProMEX: a mass spectral reference database for proteins and protein phosphorylation sites, BMC Bioinformatics. Jun. 23, 2007;8:216.
Kirkpatrick, D. S., et al., The absolute quantification strategy: a general procedure for the quantification of proteins and post-translational modifications, Methods. Mar. 2005;35(3):265-73.
Nita-Lazar, A., et al, Quantitative phosphoproteomics by mass spectrometry: past, present, and future, Proteomics. Nov. 2008;8(21):4433-43.

(Continued)

*Primary Examiner* — Shafiqul Haq
*Assistant Examiner* — Carmencita M Belei
(74) *Attorney, Agent, or Firm* — Mintz Levin Cohn Ferris Glovsky and Popeo, P.C.; Muriel Liberto, Esq.

(57) ABSTRACT

The present invention provides a method for quantifying modified peptides in a sample, the method comprising: (a) obtaining peptides from the sample; (b) adding reference modified peptides to the peptides obtained in step (a) to produce a mixture of peptides and reference modified peptides; (c) carrying out mass spectrometry (MS) on said mixture of peptides and reference modified peptides to obtain data relating to the peptides in the sample; and (d) comparing the data relating to the peptides in the sample with data in a database of modified peptides using a computer program; wherein the database of modified peptides is compiled by a method comprising: (i) obtaining peptides from a sample; (ii) enriching modified peptides from the peptides obtained in step (i); (iii) carrying out liquid chromatography-tandem mass spectrometry (LC-MS/MS) on the enriched modified peptides obtained in step (ii); (iv) comparing the modified peptides detected in step (iii) to a known reference database in order to identify the modified peptides; and (v) compiling data relating to the modified peptides identified in step (iv) into a database.

12 Claims, 16 Drawing Sheets

(56) References Cited

OTHER PUBLICATIONS

Olsen, J. V., et al., Global, in vivo, and site-specific phosphorylation dynamics in signaling networks, Cell. Nov. 3, 2006;127(3):635-48.

Pasa-Tolic, L., et al., Proteomic analyses using an accurate mass and time tag strategy, Biotechniques. Oct. 2004;37(4):621-4.

Ross, P. L., et al., Multiplexed protein quantitation in Saccharomyces cerevisiae using amine-reactive isobaric tagging reagents, Mol Cell Proteomics. Dec. 2004;3(12):1154-69.

Ruse, C. I., et al., Quantitative dynamics of site-specific protein phosphorylation determined using liquid chromatography electrospray ionization mass spectrometry, Anal Chem. Apr. 1, 2002;74(7):1658-64.

Smith, J. C., et al., Recent developments in mass spectrometry-based quantitative phosphoproteomics, Biochem Cell Biol. Apr. 2008;86(2):137-48.

Steen, H., et al., Stable isotope-free relative and absolute quantitation of protein phosphorylation stoichiometry by MS, Proc Natl Acad Sci U S A. Mar. 15, 2005;102(11):3948-53.

Wang, Y-T., et al., Semi-quantitation Strategy for Label-free Quantitative Profiling of Phosphoproteome in Lung Cancer of Different Invasive Potential, Proceedings of the 56th ASMS Conference on Mass Spectrometry and Allied Topics, Denver, CO, Jun. 1-5, 2008.

Yang, F., et al., Applying a targeted label-free approach using LC-MS AMT tags to evaluate changes in protein phosphorylation following phosphatase inhibition, J Proteome Res. Nov. 2007;6(11):4489-97.

Yi, Z., et al., Quantification of phosphorylation of insulin receptor substrate-1 by HPLC-ESI-MS/MS, J Am Soc Mass Spectrom. Apr. 2006;17(4):562-7.

Zhang, J., et al., Targeting cancer with small molecule kinase inhibitors, Nat Rev Cancer. Jan. 2009;9(1):28-39.

Zhou, H., et al., A systematic approach to the analysis of protein phosphorylation, Nat Biotechnol. Apr. 2001;19(4):375-8.

* cited by examiner

| Phosphoprotein | starved | +serum | +WM | p value (n=4) |
|---|---|---|---|---|
| IPI00761691-148-161 | | | | 6.55E-06 |
| IPI00118923 | | | | 7.07E-05 |
| IPI00118923 | | | | 7.07E-05 |
| IPI00222742-327-338 | | | | 0.00025 |
| IPI00223759-302-313 | | | | 0.000471 |
| IPI00380280-1855-1869 | | | | 0.000639 |
| IPI00338178-199-210 | | | | 0.000675 |
| IPI00117924-169-181 | | | | 0.000781 |
| IPI00469392-492-515 | | | | 0.00091 |
| IPI00664131-678-695 | | | | 0.001093 |
| IPI00128248-453-468 | | | | 0.001383 |
| IPI00117089-142-161 | | | | 0.00147 |
| IPI00222037 | | | | 0.001663 |
| IPI00128703 | | | | 0.001685 |
| IPI00128703-76-93 | | | | 0.001858 |
| IPI00467384-284-310 | | | | 0.001938 |
| IPI00123157-21-32 | | | | 0.001959 |
| IPI00317891-373-396 | | | | 0.002081 |
| IPI00266942-660-674 | | | | 0.002242 |
| IPI00323349-474-491 | | | | 0.002321 |
| IPI00656285 | | | | 0.002379 |
| IPI00114417-399-413 | | | | 0.002379 |
| IPI00357145-340-354 | | | | 0.002383 |
| IPI00420186-217-237 | | | | 0.00239 |
| IPI00268688-505-517 | | | | 0.00239 |
| IPI00421179-1076-1099 | | | | 0.002572 |
| IPI00466996-247-258 | | | | 0.002643 |
| IPI00625105-214-231 | | | | 0.003074 |
| IPI00330599 | | | | 0.003113 |
| IPI00229534-159-166 | | | | 0.003143 |
| IPI00420186-558-589 | | | | 0.003312 |
| IPI00654388-538-551 | | | | 0.003334 |
| IPI00465879 | | | | 0.003493 |
| IPI00465879-381-399 | | | | 0.003493 |
| IPI00670545-573-588 | | | | 0.003614 |
| IPI00169768-328-343 | | | | 0.003701 |
| IPI00319673-243-257 | | | | 0.0038 |
| IPI00228775-68-77 | | | | 0.003804 |
| IPI00130114 | | | | 0.004089 |
| IPI00676243-732-747 | | | | 0.004366 |
| IPI00759870-238-270 | | | | 0.004742 |
| IPI00223579-1254-1275 | | | | 0.004755 |
| IPI00318938-19-50 | | | | 0.00481 |
| IPI00169500 | | | | 0.005071 |
| IPI00172027-903-919 | | | | 0.005279 |
| IPI00751833-37-50 | | | | 0.005505 |
| IPI00130114-370-395 | | | | 0.005668 |
| IPI00154109-66-76 | | | | 0.005974 |
| IPI00135475-140-147 | | | | 0.006016 |
| IPI00318048-551-565 | | | | 0.006087 |
| IPI00454138-407-418 | | | | 0.006416 |

*FIG. 2B*

| Phosphoprotein | starved | +serum | +WM | p value (n=4) |
|---|---|---|---|---|
| Mitogen-activated protein kinase kinase 3; | | | | 0.0015 |
| Serine/threonine-protein kinase LATS2 | | | | 0.0071 |
| Serine/threonine-protein kinase PRP4 homolog | | | | 0.0078 |
| Mitogen-activated protein kinase 3 | | | | 0.0181 |
| Elongation factor 2 kinase | | | | 0.0583 |
| Isoform 1 of Serine/threonine-protein kinase N2; | | | | 0.0616 |
| Serine/threonine-protein kinase PFTAIRE-1; | | | | 0.0681 |
| Tyrosine-protein kinase-protein kinase SgK269; | | | | 0.1397 |
| Tyrosine-protein kinase ABL2; | | | | 0.1439 |
| Protein phosphatase 1 regulatory subunit 11 | | | | 0.0001 |
| Sphingosine-1-phosphate phosphatase 1; | | | | 0.0206 |
| protein tyrosine phosphatase, non-receptor type 14 | | | | 0.0234 |
| Similar to protein phosphatase 1, regulatory (inhibitor) subunit 2; | | | | 0.0298 |
| dual specificity phosphatase 6 | | | | 0.0320 |
| Protein phosphatase 2A B56 delta subunit | | | | 0.0354 |
| Protein phosphatase 2A B56 delta subunit | | | | 0.0458 |
| protein phosphatase 1, regulatory (inhibitor) subunit 2 | | | | 0.0468 |

(Protein kinases: rows 1–9; Protein phosphatases: rows 10–17)

FIG. 3

| Cell line: | FUJi-31 | HEL | CMK | KG1 | Kasumi | CTS | MV4-11 |
|---|---|---|---|---|---|---|---|
| | 1.4 | 0.6 | -0.17 | -0.51 | -1.0 | -1.4 | -1.5 |

Most resistant ← → Most sensitive

METHOD FOR QUANTIFYING MODIFIED PEPTIDES

The present invention relates to methods for quantifying modified peptides, and in particular to methods for quantifying phosphorylated peptides. Such methods are used, for example, to identify and quantify phosphorylation sites on proteins and to quantify the activity of protein kinases.

Most proteins are modified in some way by the addition of functional groups and these modifications can be detected by mass spectrometry.

Protein modifications that can be detected by mass spectrometry include phosphorylation, nitration, glycosylation, acetylation, methylation and lipidation. These protein modifications have various biological roles in the cell.

Mass spectrometry (MS) is an analytical technique that measures the mass to charge (m/z) ratio of the ions formed when a molecule or atom is ionized, vaporized and introduced into an instrument capable of separating these ions according to their m/z ratios. Mass spectrometry may also involve breaking molecules into fragments, thus enabling the structure of the molecules to be determined. The combination of MS with the physical separation technique of liquid chromatography is known as liquid chromatography-mass spectrometry (LC-MS).

In a typical MS procedure, a sample is loaded onto the MS instrument and compounds present in this sample are ionized, for example by electrospray ionization (ESI) or matrix assisted laser desorption/ionization (MALDI). The mass to charge ratio of the ions is then calculated by different forms of mass analysers such as time of flight, ion traps or quadrupoles, or combination of these.

The homeostasis of normal cells is controlled by the action of cell signalling pathways, which, when deregulated, also contribute to many diseases including cancer, neurodegeneration, allergy and diabetes. Protein and lipid kinases are prominent members of these pathways, and therefore, these enzymes represent one of the most important classes of drug targets for the treatment of many diseases.

Approaches for the unbiased detection of enzymatic activities have been reported. It is possible to use chemical probes to covalently link reactive amino acids in enzyme active sites (Blethrow, J. D. et al. *Proc Natl Acad Sci USA* 105, 1442-1447 (2008)) or on the substrates (Barglow, K. T. & Cravatt, B. F. *Nat Methods* 4, 822-827 (2007)). Proteins linked to the probes are affinity purified and their identities determined by mass spectrometry. This approach can detect activities and substrates, but it requires a large number of cells and the information provided is only qualitative.

As a more quantitative approach, quantification of phosphorylation sites on proteins known to be substrates of specific kinases serves as a measure of kinase activity. When performed using mass spectrometry as the readout, this approach allows the quantification of hundreds to thousands of phosphorylation sites in a single experiment. For example, using metabolic labelling with stable isotopes (the SILAC approach) it was possible to quantify >2000 phosphorylation sites that showed altered levels of expression upon treatment of HeLa cells with EGF (Olsen, J. V. et al. *Cell* 127, 635-648 (2006)). However, since cells need to be metabolically active to incorporate labelled amino acids, this approach cannot be used as a general tool to quantify cell signalling in primary tissues, and its low throughput limits its usefulness.

The use of isotope labelled internal standard peptides to measure phosphorylated peptides could be an alternative (Gerber, S. A. et al. *Proc Natl Acad Sci USA* 100, 6940-6945 (2003)) but, although theoretically possible, the synthesis of thousands of phosphorylated peptides labelled with stable isotopes to use as internal standards is not possible in practice.

iTRAQ reagents can be used to label peptides chemically with stable isotopes (Ross, P. L.; et al. *Mol Cell Proteomics* 2004, 3, (12), 1154-69). This technique can be used for relative quantification of peptides, including modified peptides. Its limitation is that the number of samples that can be compared is limited by the number of isotope labels, putting a limit to its usefulness for obtaining statistical validation of the data. Chemical labelling is also not practical in a clinical setting and can introduce variability at the chemical reaction step.

There is thus a need in the art for a method which can be used for unbiased, comprehensive and accurate measurement of signalling pathways in primary tissues.

The present inventors have devised an improved method for quantifying modified peptides and in particular phosphorylated peptides. The method involves the preparation of a database of modified peptides and the comparison of the database with data obtained from biological samples, typically using a computer programme.

In a first aspect, the present invention provides a method for quantifying modified peptides in a sample, the method comprising:
  (a) obtaining peptides from the sample;
  (b) adding reference modified peptides to the peptides obtained in step (a) to produce a mixture of peptides and reference modified peptides;
  (c) carrying out mass spectrometry (MS) on said mixture of peptides and reference modified peptides to obtain data relating to the peptides in the sample; and
  (d) comparing the data relating to the peptides in the sample with data in a database of modified peptides using a computer programme;
wherein the database of modified peptides is compiled by a method comprising:
  i) obtaining peptides from a sample;
  ii) enriching modified peptides from the peptides obtained in step (i);
  iii) carrying out liquid chromatography-tandem mass spectrometry (LC-MS/MS) on the enriched modified peptides obtained in step (ii);
  iv) comparing the modified peptides detected in step (iii) to a known reference database in order to identify the modified peptides; and
  v) compiling data relating to the modified peptides identified in step (iv) into a database.

The present invention provides a method for quantifying modified peptides in a sample. The method of the invention is suitable for quantifying peptides which contain any modifications which can be detected by mass spectrometry.

The method of the invention is used to quantify modified peptides which are derived from longer proteins. The method of the invention can be used to simultaneously quantify thousands of modified peptides.

The method of the invention is particularly useful for quantifying phosphorylated peptides in a sample and thus in one embodiment the modified peptides are phosphorylated peptides. In relation to this embodiment of the invention, the term "phosphoprotein" is used herein to refer to a phosphorylated protein and the term "phosphopeptide" is used herein to refer to a phosphorylated peptide.

The method of the invention is also useful for quantifying peptides that have been modified by, for example, acetylation, nitration, glycosylation, methylation and/or lipidation.

The method of the invention can be used to quantify modified peptides in any sample which contains peptides. The sample is typically a biological sample and can thus be any type of sample obtained from a biological source, for example a sample obtained from a human, animal, plant or bacterium. The invention thus encompasses the use of samples obtained from human and non-human sources.

The method of the present invention finds use in the detection and quantification of modified peptides in a sample from any species of interest. Typically, the method of the invention is used to analyse a sample from a human or animal. The animal is typically a mammal, such as a mouse, rat, guinea pig, cow, sheep or goat. The animal is alternatively a bird, such as a chicken, a fish, such as a zebra fish, a nematode, such as the worm *Caenorhabditis elegans*, or an insect, such as the fruit fly *Drosophila melanogaster*. The method of the invention can also be used to analyse samples from other life-forms such as bacteria and yeast. The method of the invention can be used to analyse samples from an experimentally important species of bacterium such as *Escherichia coli, Salmonella enterica, Streptococcus pneumoniae* or *Staphylococcus aureus*, or of yeast such as the baker's yeast *Saccharomyces cerevisiae* or the fission yeast *Schizosaccharomyces pombe*. The method of the invention can also be used to analyse a sample from a plant or fungus or a virus.

Typically, the biological sample is derived from a human, and can be, for example, a sample of a bodily fluid such as urine or blood, or another tissue. Typically, the biological sample is a cell line or a tissue; typically a primary tissue. For example, the sample can be a tissue from a human or animal. The human or animal can be healthy or diseased.

In some embodiments of the invention, the sample itself or the organism from which the sample is obtained is treated with a test substance prior to carrying out the method of the invention. Thus, in this embodiment, a cell line or an organism from which a tissue is obtained is treated with a test substance prior to carrying out the method of the invention on the cell line or tissue. The test substance is typically an exogenous chemical or drug, such as small molecule inhibitors, RNAi, therapeutic peptides, and antibodies. This embodiment of the invention allows the investigation of the effects of the test substance on peptide modification. For example, in one embodiment, where the method of the invention is used to quantify phosphorylated peptides, a cell line can be treated with agonists of pathways and/or kinase inhibitors prior to carrying out the method of the invention. Typical kinase inhibitors include inhibitors of PI3K such as wortmannin and PI-103, as used in the Examples. At least 80 kinase inhibitors are in different stages of clinical development (Zhang, J.; et al *Nat Rev Cancer* 2009, 9, (1), 28-39.) The technique is also useful to investigate other types of inhibitors suspected to have an effect on kinase pathways, such as HSP90 inhibitors, phosphatase inhibitors and antibody drugs.

Step (a) of the method of the invention involves obtaining peptides from the sample. Peptides can be obtained from the sample using any suitable method known in the art.

In one embodiment, step (a) of the method of the invention comprises:
(1) lysing cells in the sample;
(2) extracting the proteins from the lysed cells obtained in step (1); and
(3) cleaving said proteins into peptides.

In step (1) of this embodiment of the invention, the cells in the sample are lysed, or split open. The cells can be lysed using any suitable means known in the art, for example using physical methods such as mechanical lysis (for example using a Waring blender), liquid homogenization, sonication or manual lysis (for example using a pestle and mortar) or detergent-based methods such as CHAPS or Triton-X. Typically, the cells are lysed using a denaturing buffer such as a urea-based buffer.

In step (2) of this embodiment of the invention, proteins are extracted from the lysed cells obtained in step (1). In other words, the proteins are separated from the other components of the lysed cells.

In step (3) of this embodiment of the invention, the proteins from the lysed cells are cleaved into peptides. In other words, the proteins are broken down into shorter peptides. Protein breakdown is also commonly referred to as digestion. Protein cleavage can be carried out in the present invention using any suitable agent known in the art.

Protein cleavage or digestion is typically carried out using a protease. Any suitable protease can be used in the present invention. In the present invention, the protease is typically trypsin, chymotrypsin, Arg-C, pepsin, V8, Lys-C, Asp-C and/or AspN.

Alternatively, the proteins can be cleaved chemically, for example using hydroxylamine, formic acid, cyanogen bromide, BNPS-skatole, 2-nitro-5-thiocyanobenzoic acid (NTCB) or any other suitable agent.

The peptides used in the present invention and which are typically produced by protein cleavage or digestion as in step (3) described above are suitable for mass spectrometric analysis. Typically, such peptides are between about 5 and 30 amino acids long, for example from 7 to 25 amino acids, from 10 to 20 amino acids, from 12 to 18 amino acids or from 14 to 16 amino acids. However, shorter and longer peptides, such as between about 2 and about 50, for example from about 3 to about 40 or from about 4 to about 45 amino acids can also be used. The length of the peptide that can be analysed is limited by the ability of the mass spectrometer to sequence such long peptides. In certain cases polypeptides of up to 300 amino acids can be analysed.

In step (b) of the method of the invention, reference modified peptides are added to the peptides obtained from the sample to produce a mixture of peptides and reference modified peptides. Step (b) thus results in one mixture of peptides (including modified ones) per sample. The reference modified peptides are also referred to herein as "internal standards" (ISs). Typically, 5 to 10, for example 6 to 9 or 7 to 8, reference modified peptides are added.

In the present invention, the reference modified peptides are typically reference phosphorylated peptides. Such reference phosphorylated peptides are typically derived from a reference protein of defined nature and concentration, often referred to as an internal standard (IS) protein. ISs can be commercially available proteins, for example casein. Alternatively, ISs are synthesised specifically for use in the invention. In this embodiment of the invention, reference phosphorylated peptides are typically synthesised with the same sequence as some of the phosphorylated peptides that it is desired to quantify but which are enriched in stable heavy isotopes of carbon and nitrogen. The peptides are typically synthesised using solid phase chemistry in which one amino acid is added at a time to form an amino acid chain or polypeptide.

Typically, such peptides are enriched in $^{13}C$ and $^{15}N$ that substitute the common $^{12}C$ and $^{14}N$. This enrichment results in the reference phosphorylated peptides being approximately 6 to 10 daltons heavier than the endogenous phosphorylated peptides with the same sequence so that they can be distinguished using a mass spectrometer.

In another embodiment of the invention, when the method of the invention is used to quantify acetylated peptides, the reference modified peptides are reference acetylated peptides. Such reference acetylated peptides are typically synthetic peptides containing acetylated amino acids.

The reference modified peptides are typically added at a known amount in each of the samples to be compared. The signals of the endogenous modified peptides are normalised to the signal of the reference modified peptides in downstream analysis.

In one embodiment, step (b) of the method of the invention further comprises enriching modified peptides from the mixture of peptides and reference modified peptides obtained in step (b) to produce a mixture of enriched modified peptides. This additional step thus results in a single mixture of enriched modified peptides per sample. In this embodiment of the invention, step (c) thus comprises carrying out mass spectrometry (MS) on said mixture of enriched modified peptides to obtain data relating to the peptides in the sample. In this embodiment of the invention, step (b) typically results in a mixture of enriched phosphorylated peptides.

The step of enriching modified peptides is typically carried out using chromatography. In one embodiment, the chromatography is immobilized metal ion affinity chromatography (IMAC), titanium dioxide ($TiO_2$) chromatography, and/or zirconium dioxide ($ZrO_2$) chromatography. Typically, the chromatography is IMAC and $TiO_2$ chromatography.

Alternatively, the step of enriching modified peptides is carried out using antibody-based methods.

In one embodiment of the invention, when the peptides being quantified are phosphorylated peptides, antibodies with affinity to phosphorylated amino acids such as tyrosine, threonine, serine or histidine are linked (immobilised) to a solid matrix. Phosphorylated peptides are enriched by the ability of these antibodies to specifically bind phosphorylated peptides. Non-phosphorylated peptides are then washed away while phosphorylated peptides are retained on the antibody coated matrices. Elution of phosphorylated peptides from the immobilised antibody is typically carried out using low pH solvents or by any other suitable method that denatures the interaction between antibody and phosphorylated peptides.

In another embodiment of the invention, when the peptides being quantified are acetylated peptides, acetylated peptides are enriched by the use of specific antibodies against acetylated amino acid residues. Such antibodies are linked to a solid matrix and then enriched by the ability of the antibodies to specifically bind acetylated amino acid residues. Non-acetylated peptides are then washed away while acetylated peptides are retained on the immobilised antibody.

In step (c) of the method of the invention, mass spectrometry (MS) is carried out on the mixture of peptides and reference modified peptides obtained in step (b) to obtain data relating to the peptides in the sample. Typically, this data is in the form of an MS datafile for the sample. In one embodiment of the invention, when step (b) of the method of the invention further comprises enriching modified peptides from the mixture of peptides and reference modified peptides obtained in step (b) to produce a mixture of enriched modified peptides, step (c) comprises carrying out mass spectrometry (MS) on said mixture of enriched modified peptides to obtain data relating to the peptides in the sample, typically an MS datafile for the sample. Typically, the mass spectrometry is liquid chromatography-mass spectrometry (LC-MS). Step (c) thus typically results in an LC-MS datafile (one from each sample).

The data relating to the peptides in the sample typically comprises the mass to charge (m/z) ratio, charge (z) and/or relative retention time of the peptides.

In step (d) of the method of the invention, the data relating to the peptides in the sample (typically in the form of an MS datafile and more typically an LC-MS datafile) is compared with data in a database of modified peptides using a computer programme. For example, the mass to charge (m/z) ratio, charge (z) and relative retention time of the peptides in the sample are compared with the mass to charge (m/z) ratio, charge (z) and relative retention time of the modified peptides in the database. This enables the identification and quantification of each modified peptide in the sample using the database of modified peptides.

Typically, the computer programme is the programme termed PESCAL (Cutillas, P. R.; Vanhaesebroeck, B. *Mol Cell Proteomics* 6(9), 1560-73, 2007). PESCAL constructs extracted ion chromatograms (XIC, i.e, an elution profile) for each of the modified peptides present in the database across all the samples that are to be compared. This is done by centering the XIC on the m/z and retention time of the peptide previously identified to be phosphorylated (i.e, present in the database constructed in the first step of the procedure). PESCAL also considers the charge of the peptide to help in the correct assignment of identity. The program also calculates the peak height and area under the curve of each XIC. The data is normalised by dividing the intensity reading (peak areas or heights) of each modified peptide that is being analysed by those of the reference modified peptides.

In the method of the invention, the database of modified peptides is compiled by a method comprising the following steps:
 (i) obtaining peptides from a sample;
 (ii) enriching modified peptides from the peptides obtained in step (i);
 (iii) carrying out liquid chromatography-tandem mass spectrometry (LC-MS/MS) on the enriched modified peptides obtained in step (ii);
 (iv) comparing the modified peptides detected in step (iii) to a known reference database in order to identify the modified peptides; and
 (v) compiling data relating to the modified peptides identified in step (iv) into a database.

Step (i) of the method of the invention involves obtaining peptides from a sample. Peptides can be obtained from the sample using any suitable method known in the art.

The sample is typically a biological sample and can thus be any type of sample obtained from a biological source, as described above. Typically, the sample is a cell line or a primary tissue.

In some embodiments of the invention, where the sample used in step (i) is a cell line, the sample is treated with an inhibitor prior to carrying out step (i). The inhibitor can be any suitable type of inhibitor. Typically, when the method of the invention is used to quantify phosphorylated peptides, the inhibitor is a phosphatase inhibitor. Treatment with phosphatase inhibitors increases the stoichiometry of phosphorylation and results in a greater number of phosphorylated peptides that can be included in the database. In addition, methyl transferase or acetyl hydrolase inhibitors can be used when the purpose is to quantify methylated and acetylated peptides, respectively.

In one embodiment, step (i) of the method of the invention comprises:
 (1) lysing cells in a sample;
 (2) extracting the proteins from the lysed cells obtained in step (1); and
 (3) cleaving said proteins into peptides using the same method as in step (3) of step (a) described above.

In step (1) of this embodiment of the invention, the cells in the sample are lysed, or split open. The cells can be lysed using any suitable means known in the art, for example using physical methods such as mechanical lysis (for example using a Waring blender), liquid homogenization, sonication or manual lysis (for example using a pestle and mortar) or detergent-based methods such as CHAPS or Triton-X. Typically, the cells are lysed using a denaturing buffer such as a urea-based buffer.

In step (2) of this embodiment of the invention, proteins are extracted from the lysed cells obtained in step (1). In other words, the proteins are separated from the other components of the lysed cells.

In step (3) of this embodiment of the invention, the proteins from the lysed cells are cleaved into peptides using the same method as in step (3) of step (a) described above. Step (3) of step (i) thus results in a mixture of peptides including modified ones.

Protein cleavage can be carried out in the present invention using any suitable agent known in the art. However, as set out above, the method of cleavage used in step (3) of step (i) must be the same as the method of cleavage used in step (3) of step (a) described above. Protein cleavage is typically carried out using a protease. Any suitable protease can be used in the present invention. In the present invention, the protease is typically trypsin, chymotrypsin, Arg-C, pepsin, V8, Lys-C, Asp-C or AspN. Alternatively, the proteins can be cleaved chemically, for example using hydroxylamine, formic acid, cyanogen bromide, BNPS-skatole, 2-nitro-5-thiocyanobenzoic acid (NTCB) or any other suitable agent.

The peptides used in the present invention and which are typically produced by protein cleavage as in step (3) described above are suitable for mass spectrometric analysis. Typically, such peptides are between about 5 and 30 amino acids long, for example from 7 to 25 amino acids, from 10 to 20 amino acids, from 12 to 18 amino acids or from 14 to 16 amino acids. However, shorter and longer peptides, such as between about 2 and about 50, for example from about 3 to about 40 or from about 4 to about 45 amino acids can also be used. The length of the peptide that can be analysed is limited by the ability of the mass spectrometer to sequence such long peptides. In certain cases longer polypeptides, up to 300 amino acids, can be analysed.

In step (ii) of the method of the invention, modified peptides are enriched from the peptides obtained in step (i). Step (ii) thus results in several fractions enriched in modified peptides.

The enrichment of modified peptides in step (ii) is typically carried out using multidimensional chromatography. In one embodiment, the multidimensional chromatography is carried out using strong cation exchange high performance liquid chromatography (SCX-HPLC), immobilized metal ion affinity chromatography (IMAC) and titanium dioxide (TiO$_2$) chromatography. In another embodiment, the multidimensional chromatography is carried out using anion exchange high performance liquid chromatography (SAX-HPLC), immobilized metal ion affinity chromatography (IMAC) and titanium dioxide (TiO$_2$) chromatography. In these embodiments of the invention, the chromatographical techniques are carried out sequentially.

Alternatively, the enrichment of modified peptides in step (ii) is carried out using antibody-based methods.

In one embodiment of the invention, when the peptides being quantified are phosphorylated peptides, antibodies with affinity to phosphorylated amino acids such as tyrosine, threonine, serine or histidine are linked to a solid matrix. Phosphorylated peptides are enriched by the ability of these antibodies to specifically bind phosphorylated peptides. Non-phosphorylated peptides are then washed away while phosphorylated peptides are retained on the antibody coated matrix. Elution of phosphorylated peptides from the immobilized antibody is typically carried out using low pH solvents or by any other suitable method that denatures the interaction between antibody and phosphorylated peptides.

In another embodiment of the invention, when the peptides being quantified are acetylated peptides, acetylated peptides are enriched by the use of specific antibodies against acetylated amino acid residues. Such antibodies are linked to a solid matrix and then enriched by the ability of the antibodies to specifically bind acetylated amino acid residues. Non-acetylated peptides are then washed away while acetylated peptides are retained on the antibody coated matrix.

In step (iii) of the method of the invention, liquid chromatography-tandem mass spectrometry (LC-MS/MS) is carried out on the enriched modified peptides obtained in step (ii).

In step (iv) of the method of the invention, the modified peptides detected in step (iii) are compared to a known reference database in order to identify the modified peptides. This step is typically carried out using a commercially available search engine, such as, but not restricted to, the MASCOT, ProteinProspector Phenyx, or Sequest search engines.

In step (v) of the method of the invention, data relating to the modified peptides identified in step (iv) is compiled into a database. This database lists all the parameters needed for the quantification of phosphorylated peptides in subsequent biological experiments. Typically, the data relating to the modified peptides includes identity of the modified peptide, mass to charge (m/z) ratio, charge and/or relative retention time. This allows data relating to the peptides in the sample, typically the mass to charge (m/z) ratio, charge (z) and relative retention time of the peptides in the sample, to be compared to the values for the modified peptides in the database and thus allows the identification and quantification of the modified peptides in the sample.

There is no limit to the number of samples that can be compared using the method of the present invention.

The method of the present invention is typically used to quantify phosphorylated peptides. In this embodiment, the method of the invention is a technique for targeted and in-depth quantification of signalling (named TIQUAS), which allows for sensitive, rapid and comprehensive quantification of signalling pathway activity. The method can, in one simple assay, simultaneously measure the amounts of thousands of phosphorylation sites on proteins.

The method of the invention thus finds use in the analysis of signalling pathways, because the fluxes of signalling pathways are controlled to a great extent by lipid and protein kinases, enzymes which phosphorylate proteins.

The method according to this embodiment of the present invention has advantages over other methods that use mass spectrometry to quantify phosphorylated peptides (see Table 1). These advantages include comprehensiveness (thousands of phosphorylated peptides can be quantified), throughput (the analysis time is about 2 hrs/sample or about 20 samples/day/LC-MS), the ability of the technique to compare an unlimited number of samples, and its superior sensitivity (because quantification does not require identification of peptides by tandem mass spectrometry (MS/MS)). For comparison a SILAC experiment needs about three weeks to compare up to 3 samples; this is because cells need to grow in SILAC media for about two weeks and extensive separation is needed for each experiment.

REFERENCES FOR TABLE 1

1. Olsen, J. V. et al. *Cell* 127, 635-648 (2006)
2. Cutillas, P. R et al. *Mol Cell Proteomics* 4, 1038-1051 (2005)
3. Gygi, S. P. et al. *Nat Biotechnol* 17, 994-999 (1999)
4. Ross, P. L. et al. *Mol Cell Proteomics* 3, 1154-1169 (2004)
5. Gerber, S. A. et al. *Proc Natl Acad Sci USA* 100, 6940-6945 (2003)
6. Barglow, K. T. & Cravat, B. F. *Nat Methods* 4, 822-827 (2007)
7. Cutillas, P. R. et al. *Proc Natl Acad Sci USA* 103, 8959-8964 (2006)

In one embodiment, the present invention provides a method for quantifying phosphorylated peptides in a sample, as set out in FIG. 1.

In one embodiment, the present invention provides a method of quantifying phosphorylated peptides in a sample, as follows. The method is referred to herein as TIQUAS. The basis of the TIQUAS technique is the construction of a database of phosphorylated peptides that can be detected and quantified by LC-MS. This database lists all the parameters needed for the quantification of phosphorylated peptides in subsequent biological experiments including the identity of the phosphorylated peptide, mass to charge ratio (m/z), charge, and relative retention time. The database is con-

TABLE 1

| Property of the method | Method name | | | | | | |
|---|---|---|---|---|---|---|---|
|  | SILAC | PAIS | ICAT/iTRAQ | AQUA | Chemical tagging | Activity-based analysis | TIQUAS |
| Absolute quantification of cell signalling activity | NO | NO | NO | YES* | NO | YES | NO |
| Multiplex quantification of cell signalling activity | YES | YES | NO | NO | NO | YES | YES |
| Amplification of signal | NO | NO | NO | NO | NO | YES | NO |
| Number of cells needed for analysis | ~$10^7$ | ~$10^7$ | ~$10^7$ | ~$10^7$ | ~$10^7$ | 10 to 1000 | $10^6$ |
| Suitable for primary tissues/clinical analyses | NO | NO | NO | NO* | NO | YES | YES |
| Able to compare an unlimited number of samples | NO | YES | NO | YES | NO | YES | YES |
| Comprehensiveness | +++ | +++ | ++ | + | ++ | + | +++ |
| Sensitivity | ++ | ++ | + | ++ | + | +++++ | +++ |
| Throughput | + | + | + | ++ | + | +++ | +++ |
| Suitable for the discovery of new activities | YES | YES | YES | NO | YES | NO | YES |
| Reference | 1 | 2 | 3, 4 | 5 | 6 | 7 | This study |

*AQUA may be suitable for the analysis of phosphorylated peptides from primary tissues when the target protein is highly abundant, but it is not suitable for the quantification of phosphorylated peptides because these are normally present in low copy numbers In one embodiment, the present invention provides a method for quantifying phosphorylated peptides in a sample, the method comprising:
(a) obtaining peptides from the sample;
(b) optionally, adding reference phosphorylated peptides to the peptides obtained in step (a) to produce a mixture of peptides and reference phosphorylated peptides and enriching phosphorylated peptides from the mixture of peptides and reference phosphorylated peptides obtained in step (b) to produce a mixture of enriched phosphorylated peptides;
(c) carrying out mass spectrometry (MS) on said mixture of peptides and reference phosphorylated peptides or said mixture of enriched phosphorylated peptides to obtain data relating to the peptides in the sample; and
(d) comparing the data relating to the peptides in the sample with data in a database of phosphorylated peptides using a computer programme;
wherein the database of phosphorylated peptides is compiled by a method comprising:
(i) obtaining peptides from a sample;
(ii) enriching phosphorylated peptides from the peptides obtained in step (i);
(iii) carrying out liquid chromatography-tandem mass spectrometry (LC-MS/MS) on the enriched phosphorylated peptides obtained in step (ii);
(iv) comparing the phosphorylated peptides detected in step (iii) to a known reference database in order to identify the phosphorylated peptides; and
(v) compiling data relating to the phosphorylated peptides identified in step (iv) into a database.

structed by enriching phosphorylated peptides using multidimensional chromatography (such as strong cation exchange, IMAC and $TiO_2$). Fractions of enriched phosphorylated peptides are then analysed by LC-MS/MS for identification of phosphorylated peptides. Constructing the database takes about 2 to 3 weeks of mass spectrometry time but once it is constructed it can be used to perform biological experiments with good throughput and sensitivity.

The inventors have written a computer program named PESCAL (Cutillas and Vanhaesebroeck, *Molecular & Cellular Proteomics* 6, 1560-1573 (2007)) that automates the quantification of each of the phosphorylated peptides listed in the database in LC-MS runs of phosphorylated peptides taken from biological experiments. For these biological experiments, proteins in cell lysates are digested using trypsin or other suitable proteases. Phosphopeptide internal standards, which are reference phosphorylated peptides, are spiked at known amounts in all the samples to be compared. Phosphorylated peptides in the resultant peptide mixture are enriched using a simple-to-perform IMAC or $TiO_2$ extraction step. Enriched phosphorylated peptides are analysed in a single LC-MS run of about 120 minutes (total cycle). PESCAL then constructs extracted ion chromatograms (XIC, i.e, an elution profile) for each of the phosphorylated peptides present in the database across all the samples that are to be compared. The program also calculates the peak height and area under the curve of each XIC. The data is normalised by dividing the intensity reading (peak areas or heights) of each phosphopeptide analyte by those of the phosphopeptide ISs.

This phosphoproteomic approach allows the comparison of an unlimited number of samples and replicates.

In another embodiment, the method of the invention is a method for quantifying acetylated peptides in a sample. Quantitative analysis of acetylation involves digesting proteins in a cell lysate with a suitable protease, for example trypsin, to generate thousands of peptides. Acetylated peptides are then enriched by the use of specific antibodies against acetylated amino acid residues. Synthetic peptides containing acetylated amino acids are used as internal standards that are spiked into the samples prior to the enriching step. LC-MS/MS is then used to identify these acetylated peptides, which are then incorporated into a database. Acetylated peptides are identified in individual samples by LC-MS, taking the entries in the database as a reference.

The present invention will now be further described by way of reference to the following Examples which are present for the purposes of illustration only. In the Examples, reference is made to a number of Figures in which:

FIG. 1 is a flowchart illustrating an embodiment of the present invention. Notes to the flowchart are as follows: [1] Treatment with phosphatase inhibitors increases the stoichiometry of phosphorylation and results in a greater number of phosphorylated peptides that can be included in the database. [2] Proteases are typically trypsin, chymotrypsin, Arg-C, pepsin, V8, Lys-C, Asp-C or AspN. [3] Multidimensional chomatography is typically carried out using strong cation exchange, high performance liquid chromatography (HPLC), immobilized metal ion affinity chromatography (IMAC) and titanium dioxide ($TiO_2$) chromatography or alternatively using anion exchange, high performance liquid chromatography (HPLC), immobilized metal ion affinity chromatography (IMAC) and titanium dioxide ($TiO_2$) chromatography. In another alternative, antibody-based methods can be used. [4] Biological samples can be any suitable biological sample and are typically cell lines (optionally treated with investigative agents) or primary tissues from animals or patients. There is no limit to the number of samples that can be compared. [5] The internal standards are reference phosphorylated peptides and are added at a known amount to each of the samples to be compared. The signals of the endogenous phosphorylated peptides are normalised to the signal of the internal standard peptides in downstream analysis.

FIG. 2 shows a strategy for quantitative analysis of cell signalling using TIQUAS in which: (A) shows experimental design; (B) gives a summary of data obtained (4 independent biological replicates), and a snapshot of the data sorted by probability; (C) is an example of extracted ion chromatograms (XIC) of a phosphorylated peptide from protein phosphatase 1 (PP1) regulatory subunit 11; (D) shows examples of phosphorylation sites on proteins previously demonstrated to be downstream of PI3K.

FIG. 4 (A) shows IC50 inhibition of proliferation by PI-103 in cell lines with differing sensitivities to PI-103; and (B) shows the results of quantification of phosphopeptides in the same cell lines using the method of the present invention. The table shows phosphopeptides with a positive correlation (high phosphorylation in more resistant cell lines).

FIG. 5 shows a strategy for accurate phosphopeptide quantification by label-free LC-MS. (A) MS Spectra showing mitogen-activated protein kinase 3 (pERK1) peptide (IADPEHDHTGFLTEpYVATR) at m/z=751.33939, tR=54.54 min, z=3). (B) The extracted ion chromatogram (XIC) of this m/z 25 ppm yields four possible candidates. (C) After applying additional charge and isotope distribution restrictions, the chromatographic elution peak of this peptide can be unequivocally identified (arrowed in the figure) since the XICs for the first three isotopes have relative intensities that correspond to those shown in the spectrum (the relative intensities of the isotopes can also be calculated from sequence data). (D) Further specificity is achieved by narrowing the mass window (±7 ppm) at which the XIC is constructed.

FIG. 6 shows that AML cell lines with different sensitivity to signaling inhibitors showed markedly different patterns of protein phosphorylation. (A), (B) and (C) AML cell lines were cultured in the presence of the indicated inhibitors for 72 h and survival measured by MTS assay. Data points are shown as the mean±SEM (n=3) (D), (E) and (F) Examples of phosphopeptides identified by TIQUAS to be robustly (as assessed by fold change) and significantly (as assessed by t-test statistics) differentially regulated in cell lines with different sensitivities to the signaling inhibitors named in (A), (B) and (C).

EXAMPLE 1

Study on PI3K Signalling

The novel quantitative techniques of the invention were used to quantify phosphorylation sites in NIH-3T3 fibroblasts, which were starved and then stimulated with serum with or without pre-incubation with the pan-PI3K inhibitor wortmannin (WM). These experiments were performed 4 times.

Figure 1:
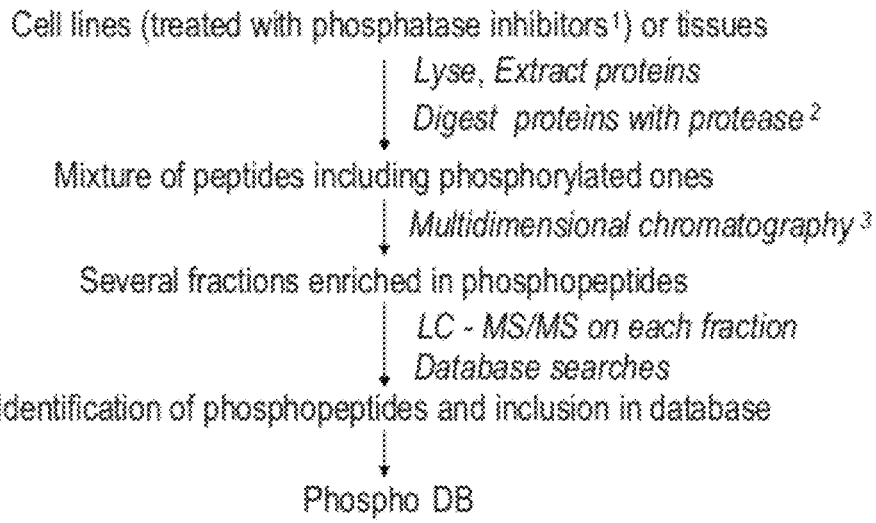
Figure 1:
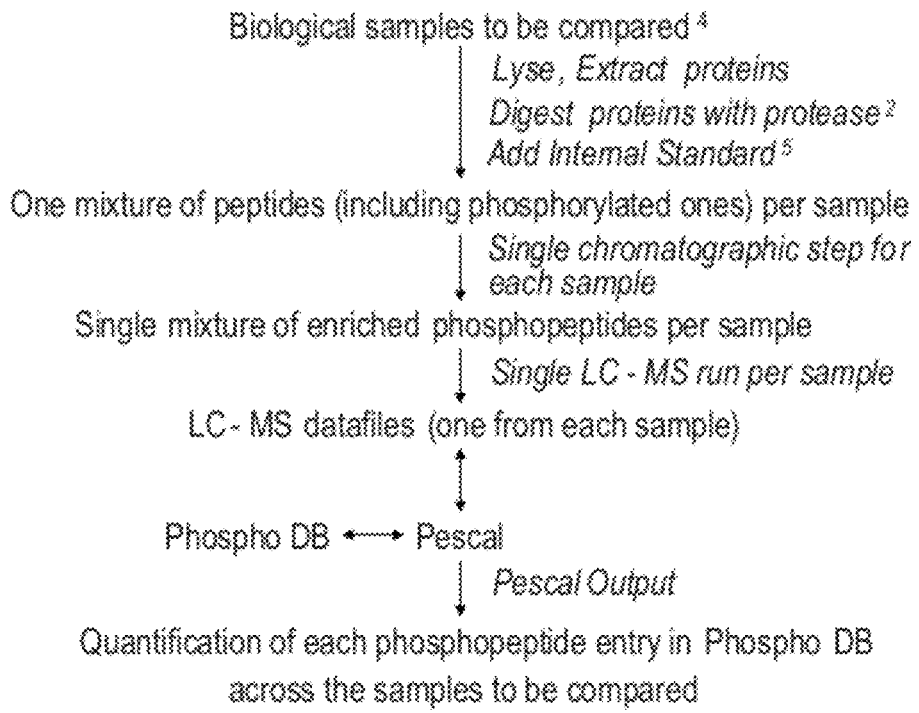
Figure 2A:
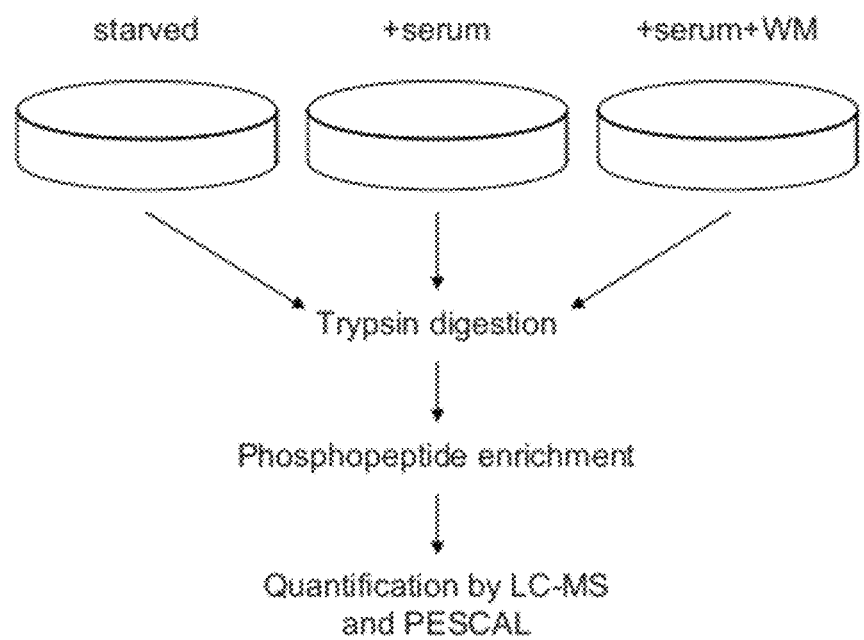

FIG. 2(A) shows experimental design. Cells were treated as indicated, lysed with a urea-based buffer to obtain nuclear as well as cytosolic proteins and proteins digested. Resultant phosphorylated peptides were enriched by IMAC and $TiO_2$ chromatography and quantified by LC-MS using a computer program developed by the inventors (PESCAL) (Cutillas and Vanhaesebroeck, *Molecular & Cellular Proteomics* 6, 1560-1573 (2007)).

FIG. 2(B) gives a summary of the data obtained and a snapshot of the data sorted by probability. 3,100 phosphopeptides were detected in the database, 2,350 phosphorylated peptides were quantified in these analyses, 265 of which were significantly (p<0.05) affected by WM treatment of cells prior to serum stimulation. Further information on the phosphopeptides shown in FIG. 2(B) is given in Table 2.

TABLE 2

| Phosphoprotein | | Phosphosite | |
|---|---|---|---|
| IPI00761691-148-161 | 27 kDa protein | VVAAALSSPVEAAK | Phospho (ST) |
| IPI00118923 | Protein phosphatase 1 regulatory subunit 11 | CCCIYEKPR | Phospho (Y) |
| IPI00118923 | Protein phosphatase 1 regulatory subunit 11 | CCCIYEKPR | Phospho (Y) |

TABLE 2-continued

| Phosphoprotein | | Phosphosite | |
|---|---|---|---|
| IPI00222742-327-338 | Adult male corpora quadrigemina cDNA, RIKEN full-length enriched library, clone: B230341L19 product: hypothetical RhoGAP domain/Pleckstrin homology (PH) domain containing protein, full insert sequence | GEPGSPGLPTHR | Phospho (ST) |
| IPI00223759-302-313 | Isoform 1 of Vacuolar protein sorting-associated protein 26B | SMSHQAAIASQR | Phospho (ST) |
| IPI0380280-1855-1869 | carbamoyl-phosphate synthetase 2, aspartate transcarbamylase, and dillydroorotase | IHRASDPGLPAEEPK | Phospho (ST) |
| IPI00338178-199-210 | Fos-related antigen 2 | RSPPTSGLQSLR | Phospho (ST) |
| IPI00117924-169-181 | histocompatibility 2, M region locus 3 | SRLESAGTAEYFR | Phospho (ST) |
| IPI00469392-492-515 | Isoform 1 of Reticulon-4; | TSNPFLVAIHDSEADYVTTDNLSK | Phospho (Y) |
| IPI00664131-678-695 | CLASP1 isoform 14 | SSSPGKLLGSGLAGGSSR | Phospho (ST) |
| IPI00126248-453-468 | Adult male testis cDNA, RIKEN full-length enriched library, clone: 4922505F07 product: ATP citrate lyase, full insert sequence | TASFSESRADEVAPAK | Phospho (ST) |
| IPI00117089-142-161 | Mitogen-activated protein kinase kinase kinase 3 | IKPSQSAGDINTIYQAPEPR | Phospho (Y) |
| IPI00222037 | melanoma inhibitory activity 3 | SSSPAKAVDEGKVNMAPK | Phospho (ST) |
| IPI00128703 | Isoform Alpha of Paxillin | YAHQQPPSPLPVYSSSAK | Phospho (ST); Phospho (Y) |
| IPI00128703-76-93 | Isoform Alpha of Paxillin | YAHQQPPSPLPVYSSSAK | Phospho (ST); Phospho (Y) |
| IPI00467384-284-310 | Isoform 1 of ADP-ribosylation factor-binding protein GGA2 | LASDTTDDDDALAEILQANDLLTQGVR | Phospho (ST) |
| IPI00123157-21-32 | BTB/POZ domain-containing protein KCTD10 | TTSFKGASPSSK | Phospho (ST) |
| IPI00317891-373-396 | Pinin | EGEKQQDSQPEEVMDVLEMVESVK | Phospho (ST) |
| IPI00266942-660-674 | Isoform 1 of Protein FAM62B | SSSSLLASPSHIAAK | Phospho (ST) |
| IPI00323349-474-491 | Tight junction protein ZO-2 | VFLRPSPEDEAIYGPNTK | Phospho (Y) |
| IPI00656285 | Forkhead box protein K1 | SAPASPTHPGLMSPR | Phospho (ST) |
| IPI00114417-399-413 | 66 kDa protein | SAPASPTHPGLMSPR | Phospho (ST) |
| IPI00357145-340-354 | similar to interferon regulatory factor 2 binding protein 2 isoform 1 | RKPSPEPEGEVGPPK | Phospho (ST) |
| IPI00420186-217-237 | Isoform 2 of Epidermal growth factor receptor substrate 15-like 1 | TVFAGAVPVLPASPPPKDSLR | Phospho (ST) |
| IPI00268688-505-517 | CD2-associated protein | FNGGHSPTQSPEK | Phospho (ST) |
| IPI00421179-1076-1099 | Isoform 1 of Eukaryotic translation initiation factor 4 gamma 1 | ITKPGSIDSNNQLFAPGGRLSWGK | Phospho (ST) |
| IPI00468996-247-258 | Neural Wiskott-Aldrich syndrome protein; | ETSKVIYDFIEK | Phospho (Y) |
| IPI00625105-214-231 | Isoform 1 of U1 small nuclear ribonucleo-protein 70 kDa | YDERPGPSPLPHR | Phospho (ST) |

TABLE 2-continued

| Phosphoprotein | | Phosphosite | |
|---|---|---|---|
| IPI00330599 | Protein LYRIC | KREEAAPPTPAPDDLAQLK | Phospho (ST) |
| IPI00229534-159-166 | Myristoylated alanine-rich C-kinase substrate | LSGFSFKK | Phospho (ST) |
| IPI00420186-558-589 | Isoform 2 of Epidermal growth factor receptor substrate 15-like 1 | SLEQYDQVPDGVSGTSLPDLATLNEGILLAER | Phospho (Y) |
| IPI00654388-538-551 | Isoform 1 of Leucine-rich repeat flightless-interacting protein 1 | SEQQAEALDSPQKK | Phospho (ST) |
| IPI00465879 | Isoform 1 of Nuclear-interacting partner of ALK | SMGTGDSAGVEVPSSPLRR | Oxidation (M); Phospho (ST) |
| IPI00465879-381-399 | Isoform 1 of Nuclear-interacting partner of ALK | SMGTGDSAGVEVPSSPLRR | Oxidation (M); Phospho (ST) |
| IPI00670545-573-588 | similar to 1a related protein isoform 1 | AVTPVPTKTEEVSNLK | Phospho (ST) |
| IPI00169768-328-343 | WAS/WASL interacting protein family member 1 | NLSLTSSAPPLPSPGR | Phospho (ST) |
| IPI00319673-243-257 | Isoform 1 of Lipin-2 | SDSELEVKPSESLLR | Phospho (ST) |
| IPI00228775-68-77 | Serpin B13 | IKSEEEEIEK | Phospho (ST) |
| IPI00130114 | mRNA decapping enzyme 1A | QKSPLLNQPVPELSHSSLVASQSPFR | Gln->pyro-Glu (N-term Q); Phospho (ST) |
| IPI00676243-732-747 | Microtubule-associated protein 1 A | GEKELSSEPR | Phospho (ST) |
| IPI00759870-238-270 | Isoform 4 of Heterogeneous nuclear ribonucleoproteins C1/C2 | MESEAGADDSAEEGDLLDDDDNEDRGDDQLELK | Phospho (ST) |
| IPI00223579-1254-1275 | Isoform 1 of Rho guanine nucleotide exchange factor 10 | NDLSSSSGSLNLSHGSSSLEHR | Phospho (ST) |
| IPI00318938-19-50 | Eukaryotic translation initiation factor 4E-binding protein 1 | RVALGDGVQLPPGDYSTTPGGTLFSTTPGGTR | 2 Phospho (ST) |
| IPI00169500 | Isoform 1 of Ataxin-2-like protein | SAAPAPVSASCPEPPIGSAVASSASIPVTSSVVDPGAGSISPASPK | Phospho (ST) |
| IPI00172027-903-919 | MKL/myocardin-like protein 2 | SGEISFPIKEEPSPISK | Phospho (ST) |
| IPI00751833-37-50 | Vimentin | TYSLGSALRPSTSR | Phospho (Y) |
| IPI00130114-370-395 | mRNA decapping enzyme 1A | QKSPLLNQPVPELSHSSLVASQSPFR | Phospho (ST) |
| IPI00154109-66-76 | Protein FAM122A | HGLLLPASPVR | Phospho (ST) |
| IPI00135475-140-147 | Isoform A of Drebrin | LSSPVLHR | Phospho (ST) |
| IPI00318048-551-565 | Nucleolar protein Nop56 | KFSEEPEVAANFTK | Phospho (ST) |
| IPI00454138-407-418 | 0 day neonate eyeball cDNA, RIKEN full-length enriched library, clone: E130120C15 product: CDNA FLJ31417 FIS, CLONE NT2NE2000327, WEAKLY SIMILAR TO GLUCOAMYLASE S1/S2 (EC 3.2.1.3) homolog | VVPQQITHTSPR | Phospho (ST) |

Figure 2C:
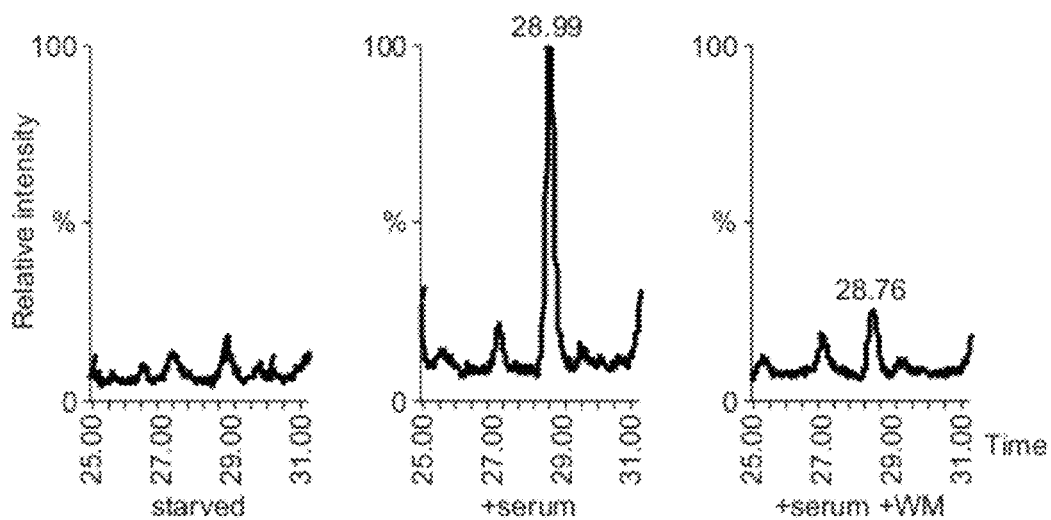

FIG. 2(C) is an example of extracted ion chromatograms (XIC) of a phosphorylated peptide from PP1 regulatory subunit 11 (CCCIpYEKPR; XIC=m/z 683.26), demonstrating that this site is sensitive to WM.

Figure 2D:
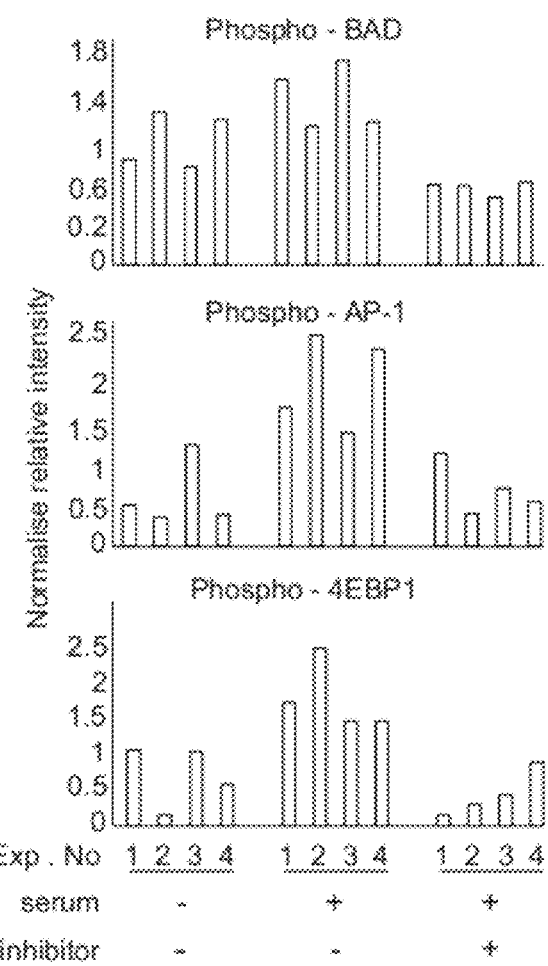

FIG. 2(D) shows examples of phosphorylation sites on proteins previously demonstrated to be downstream of PI3K. The data of the 4 independent experiments are shown separately to demonstrate the reproducibility of the experiments. These sites are known to be downstream of PI3K and thus these data validate the method of the present invention. This phosphoproteomic approach allows the comparison an unlimited number of samples and replicates.

Figure 3:
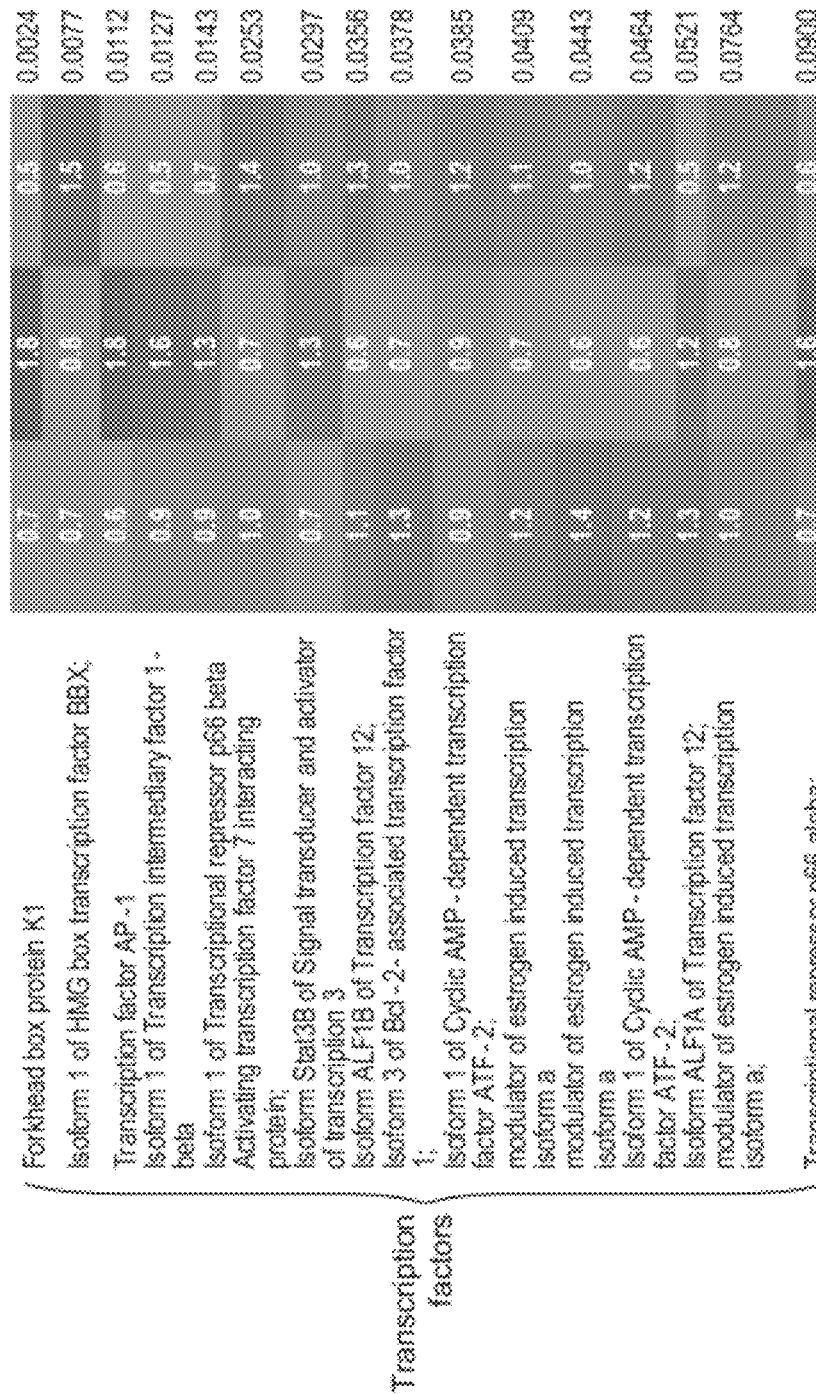
FIG. 3 shows examples of phosphorylated sites identified in the analyses described in Example 1.
Figure 3:
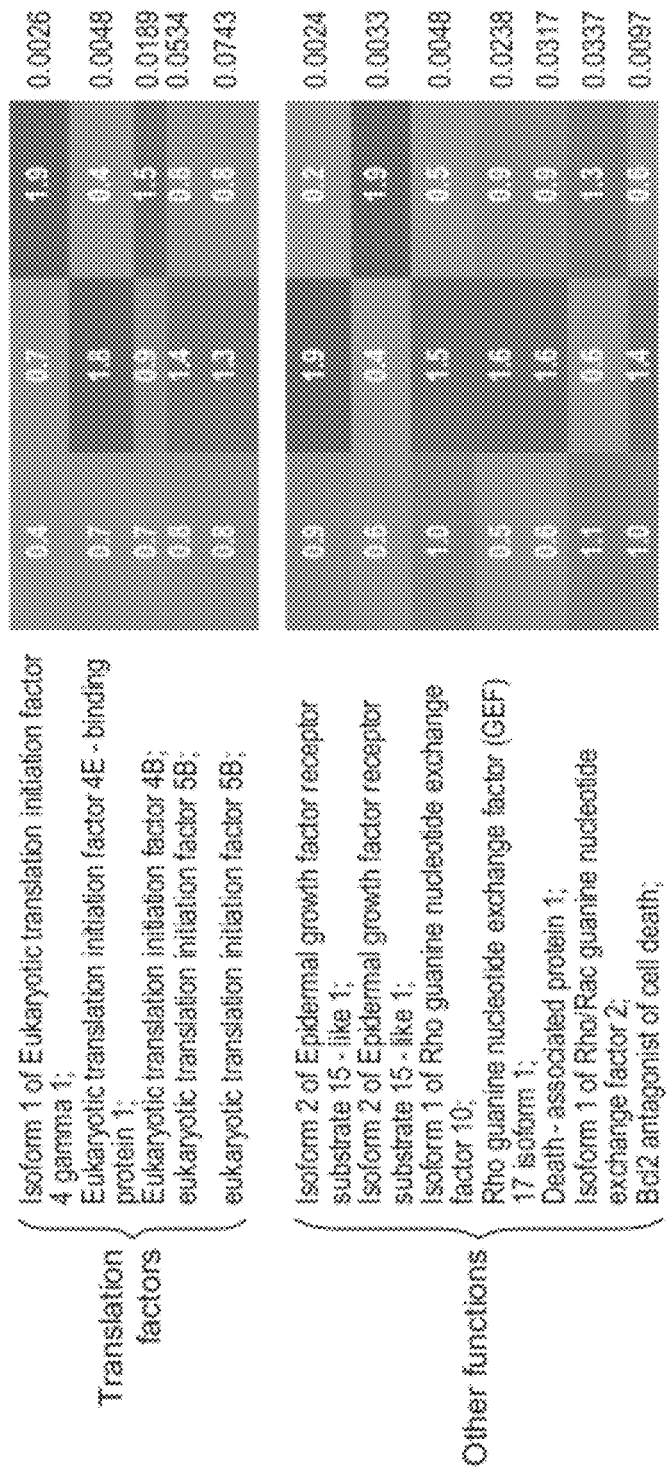
Figure 5A:
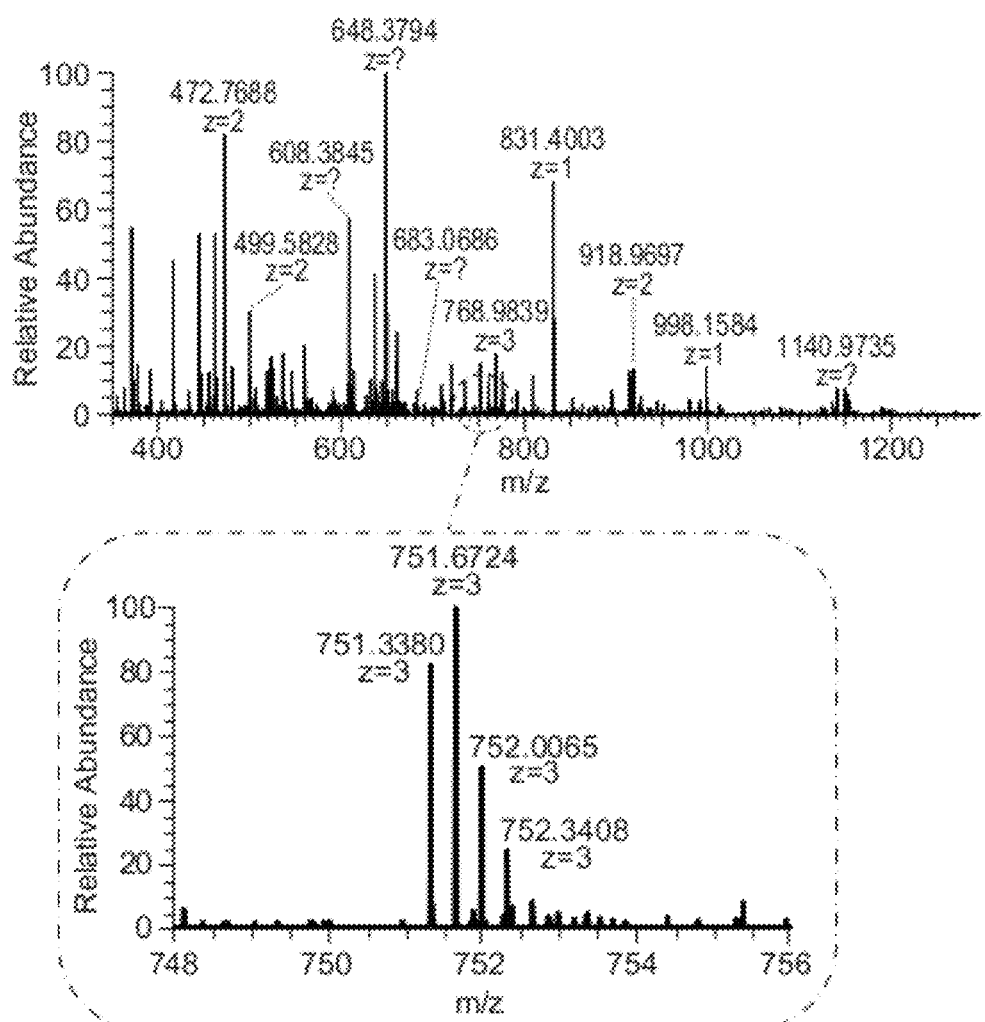
Figure 5B:
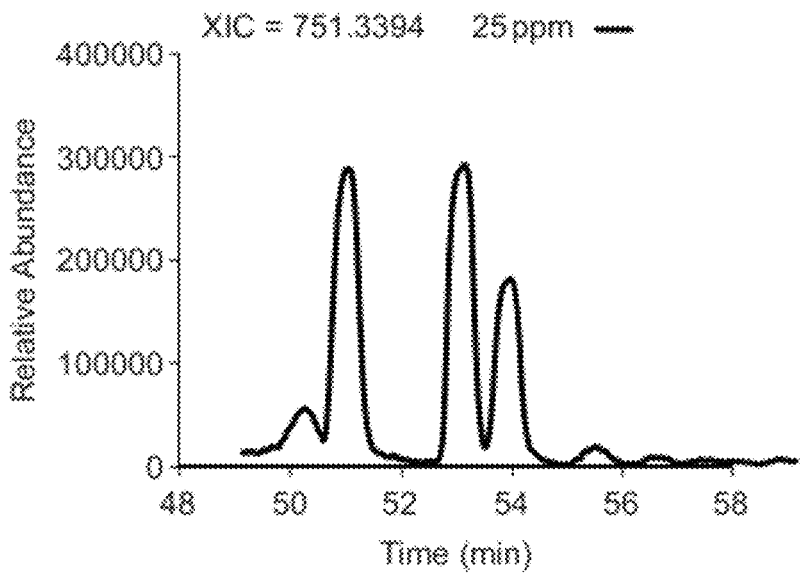
Figure 5C:
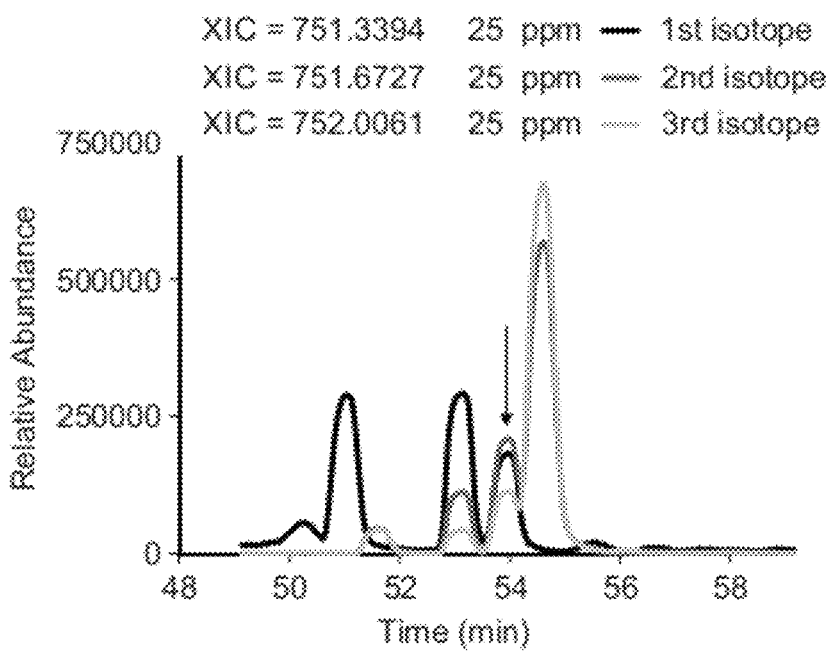
Figure 5D:
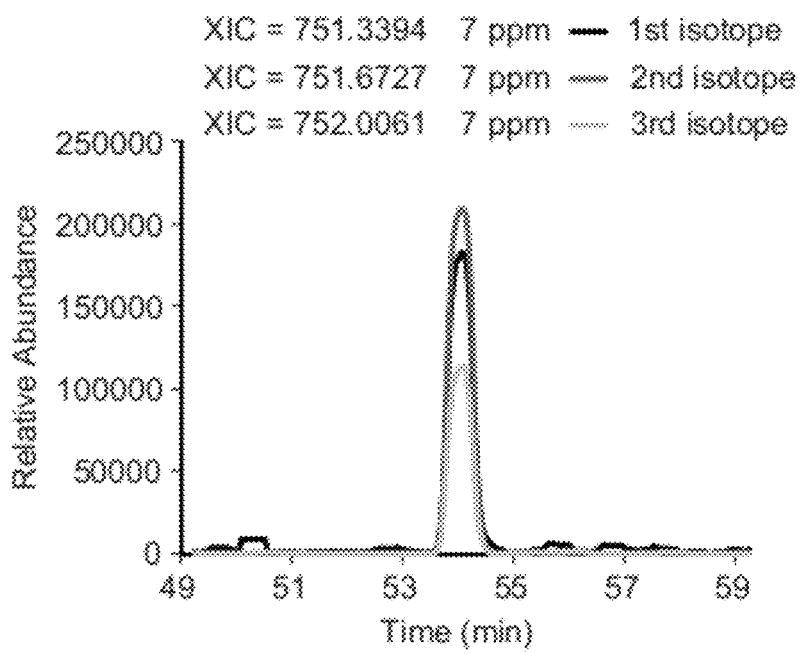

Several sites of phosphorylation were identified on protein kinases and phosphatases, and transcription and translation factors that were affected by WM treatment of cells (FIG. 3). Values are the normalized mean phosphorylated peptide levels of 4 independent experiments. The p values were calculated using the student's t test on the means of serum versus WM sample groups. Further information on the phosphopeptides shown in FIG. 3 is given in Table 3.

TABLE 3

| Phosphoprotein | Phosphopeptide | |
|---|---|---|
| Mitogen-activated protein kinase kinase kinase 3; | IKPSQSAGDINTIYQAPEPR | Phospho (Y) |
| Serine/threonine-protein kinase LATS2 | MRPKTFPATTYSGNSR | Oxidation (M); Phospho (ST) |
| Serine/threonine-protein kinase PRP4 homolog | EVIEASDKEGLSPAKR | Phospho (ST) |
| Mitogen-activated protein kinase 3 | IADPEHDHTGFLTEYVATR | Phospho (Y) |
| Elongation factor 2 kinase | TLSSSRPPLLLR | Phospho (ST) |
| Isoform 1 of Serine/threonine-protein kinase N2; | SKSEYELSIPDSGR | Phospho (Y) |
| Serine/threonine-protein kinase PFTAIRE-1; | TQSTFDPFEKPANQVK | Phospho (ST) |
| Tyrosine-protein kinase-protein kinase SgK269; | SAPTSPTATNISSK | Phospho (ST) |
| Tyrosine-protein kinase ABL2; | LMTGDTYTAHAGAK | Phospho (Y) |
| Protein phosphatase 1 regulatory subunit 11 | CCCIYEKPR | Phospho (Y) |
| Sphingosine-1-phosphate phosphatase 1; | RNSLTGEEGELVK | Phospho (ST) |
| protein tyrosine phosphatase, non-receptor type 14 | YVSGSSPDLVTR | Phospho (ST) |
| Similar to protein phosphatase 1, regulatory (Inhibitor) subunit 2; | TSAASPPVVPSAEQPRPIVEEELSKK | Phospho (ST) |
| dual specificity phosphatase 6 | SNISPNFNFMGQLLDFER | Oxidation (M); Phospho (ST) |
| Protein phosphatase 2A B56 delta subunit | RKSELPQDVYTIK | Phospho (ST) |
| Protein phosphatase 2A B56 delta subunit | RKSELPQDVYTIK | Phospho (ST) |
| protein phosphatase 1, regulatory (inhibitor) subunit 2 | WDEMNILATYHPADKDYGLMK | Phospho (Y) |
| Forkhead box protein K1 | SAPASPTHPGLMSPR | Phospho (ST) |
| Isoform 1 of HMG box transcription factor BBX; | TADGRVSPAGGTLDDKPK | Phospho (ST) |
| Transcription factor AP-1 | LQALKEEPQTVPEMPGETPPLSPIDMESQER | Phospho (ST) |
| Isoform 1 of Transcription intermediary factor 1- beta | RPAASSAAAASAAASSPAGGGGEAQELLEHCGVCR | Phospho (ST) |
| Isoform 1 of Transcriptional repressor p66 beta | LTPSPDIIVLSDNEASSPR | Phospho (ST) |
| Activating transcription factor 7 interacting protein; | RQESPPNPPISPGKPANDTNSNNNMTYR | Phospho (ST) |

TABLE 3-continued

| Phosphoprotein | Phosphopeptide | |
|---|---|---|
| Isoform Stat3B of Signal transducer and activator of transcription 3 | YCRPESQEHPEADPGSAAPYLK | Phospho (Y) |
| Isoform ALF1B of Transcription factor 12; | AGGQAPSSPSYENSLHSLK | Phospho (ST) |
| Isoform 3 of Bcl-2-associated transcription factor 1; | RIDISPSALR | Phospho (ST) |
| Isoform 1 of Cyclic AMP-dependent transcription factor ATF-2; | KMPLDLSPLATPIIR | Phospho (ST) |
| modulator of estrogen induced transcription isoform a | AGAGMITQHSSTASPVNR | Phospho (ST) |
| modulator of estrogen induced transcription isoform a | ISSKSPGHMVILNQTK | Phospho (ST) |
| Isoform 1 of Cyclic AMP-dependent transcription factor ATF-2; | MPLDLSPLATPIIR | Phospho (ST) |
| Isoform ALF1A of Transcription factor 12; | AGGQAPSSPSYENSLHSLQSR | Phospho (ST) |
| modulator of estrogen induced transcription isoform a; | AGAGMITQHSSTASPVNR | Phospho (ST) |
| Transcriptional repressor p66 alpha; | EATAQKPTASSGSTVTTPPPLVR | Phospho (ST) |
| Isoform 1 of Eukaryotic translation initiation factor 4 gamma 1; | ITKPGSIDSNNQLFAPGGRLSWGK | Phospho (ST) |
| Eukaryotic translation initiation factor 4E-binding protein 1; | RVALGDGVQLPPGDYSTTPGGTLFSTTPGGTR | 2 Phospho (ST) |
| Eukaryotic translation initiation factor 4B; | SQSSDTEQPSPTSGGGK | Phospho (ST) |
| eukaryotic translation initiation factor 5B; | SVPTVDSGNEDDDSSFK | Phospho (ST) |
| eukaryotic translation initiation factor 5B; | TARPNSEAPLSGSEDADDSNKLSK | 2 Phospho (ST) |
| Isoform 2 of Epidermal growth factor receptor substrate 15-like 1; | TVFAGAVPVLPASPPPKDSLR | Phospho (ST) |
| Isoform 2 of Epidermal growth factor receptor substrate 15-like 1; | SLEQYDQVPDGVSGTSLPDLATLNEGILLAER | Phospho (Y) |
| Isoform 1 of Rho guanine nucleotide exchange factor 10; | NDLSSSSGSLNLSHGSSSLEHR | Phospho (ST) |
| Rho guanine nucleotide exchange factor (GEF) 17 isoform 1; | DSPSAGSPMEQSESTLSQSPTSPTTRPTLK | Phospho (ST) |
| Death-associated protein 1; | DKDDQEWESTSPPKPTVFISGVIAR | Phospho (ST) |
| Isoform 1 of Rho/Rac guanine nucleotide exchange factor 2; | ERPTSAIYPSDSFR | Phospho (ST) |
| Bcl2 antagonist of cell death; | RMSDEFEGSFK | Phospho (ST) |

EXAMPLE 2

Investigation of Signalling Pathways in Cells with a Range of Sensitivities to a Dual Inhibitor of PI3K and mTOR The claimed techniques were also used to profile kinase pathways in a panel of cell lines with a range of sensitivities to PI-103, an inhibitor of the lipid kinase PI3K and the protein kinase mTOR.

The cell lines in the panel shown in FIG. 4A were incubated with a titration of PI-103 and their rate of proliferation measured as a function of inhibitor concentration. The inhibitor concentration was expressed as IC50 (concentration of inhibitor giving 50% inhibition) in micromolar units of concentration (FIG. 4A).

Figure 4B:
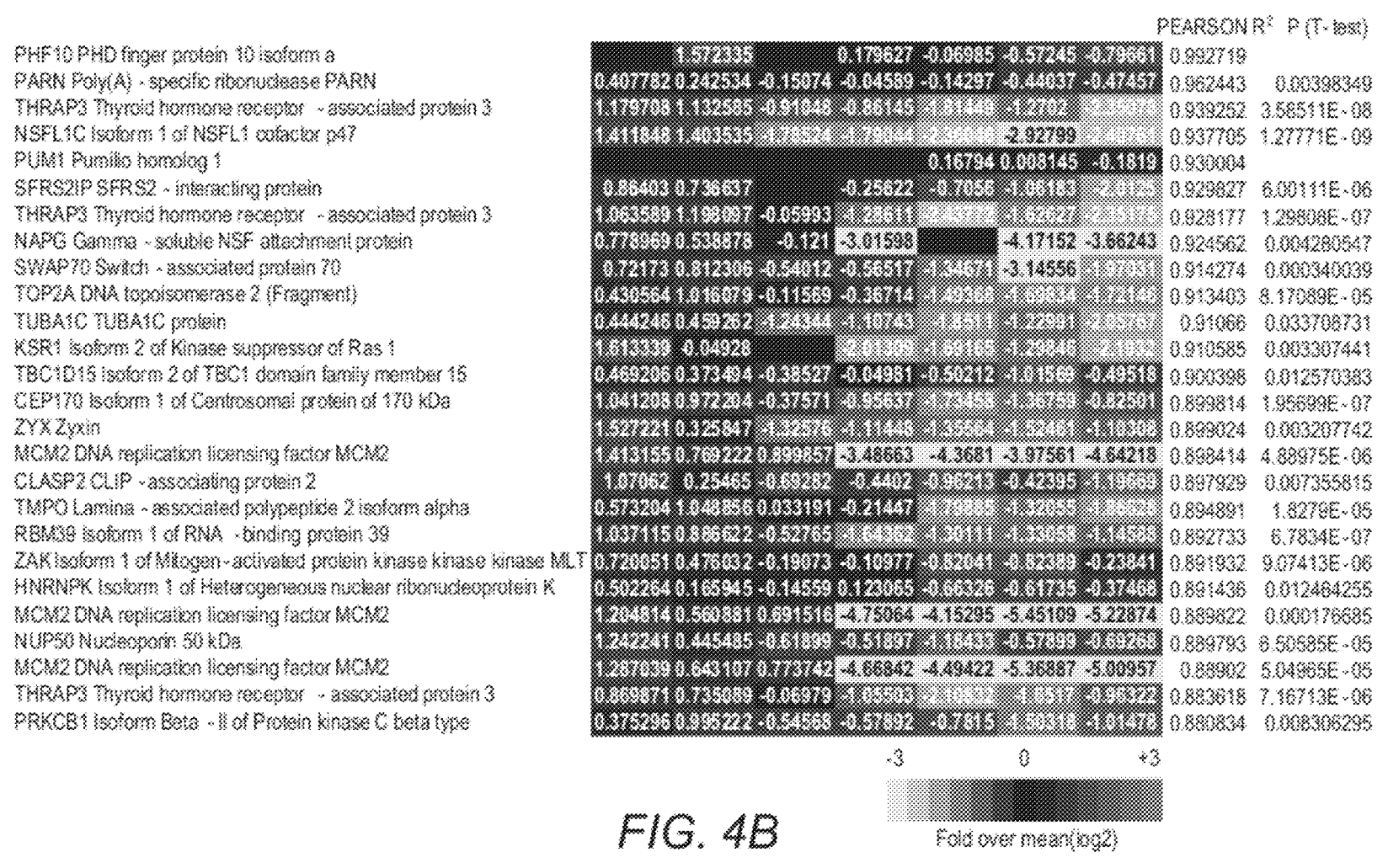

In a separate experiment (FIG. 4B), phosphopeptides in these cell lines were quantified using the disclosed techniques. Experiments were performed three times. As FIG. 4B illustrates, several phosphopeptides correlated with the IC50 values, thus suggesting a causal relationship of inhibitor efficacy with kinase pathway activation. These values correlated with statistical significance ($R^2$ values above 0.75 were statistically significant). In addition, statistical tests (student's t-test) of the mean phosphopeptide signals of resistant and sensitive cell lines were also significant.

These phosphopeptides may represent novel biomarkers of inhibitor efficacy and may also shed light into the mode of action of these inhibitors.

EXAMPLE 3

Investigation of Kinase Pathway Activation Associated with Sensitivity of Cancer Cells to Kinase Inhibitors Analytical Strategy The TIQUAS approach used in this Example consists of using LC-MS for targeting the quantification of phosphopeptides previously identified by LC-MS/MS. This analysis is automated using the computer programme PESCAL described herein (Cutillas, P. R.; Vanhaesebroeck, B. *Mol Cell Proteomics* 6(9), 1560-73, 2007). PESCAL performs extracted ion chromatograms (XIC) of the first three isotopes of a given molecular ion. This allows both the identification of the charge of the peptide ions and the calculation of the relative intensities of the isotopes that can then be correlated with theoretical isotope distributions.

FIG. 5 illustrates the principle of the analysis, which combines high resolution and high mass accuracy mass spectrometry with a new version of Pescal for specific and reliable identification of chromatographic peaks for label-free quantification. Since this is a targeted approach in which samples are analyzed by a single LC-MS/MS run, problems with undersampling in data-dependent experiments are avoided. A feature of the approach is its ability to provide in-depth quantitative information across an unlimited number of samples and replicates with sufficient throughput for its use as a routine phosphoproteomics tool, TIQUAS Analysis of Drug Response in Leukaemia Cells The responses of eight AML cell lines to a panel of inhibitors for kinases in pathways critical for AML development, namely the JAK, MEK and PI3K pathways, were investigated. Cells were treated with increasing concentrations of LY294002, PI103 and IC87114 (inhibitors that have PI3K as main targets), a MEK inhibitor (MEK I, Calbiochem), a JAK inhibitor (JAK I, Calbiochem) and a FLT3 inhibitor (Calbiochem). These kinases are all potential drug targets for the treatment of diverse forms of cancer; however the mechanisms responsible for making cells susceptible to their inhibition are poorly understood. Proliferation of the cell lines in our panel as a function of these kinase inhibitors showed a wide range of sensitivities, reflecting the clinical situation where patients may respond to cancer drugs to different extents.

Figure 6A:
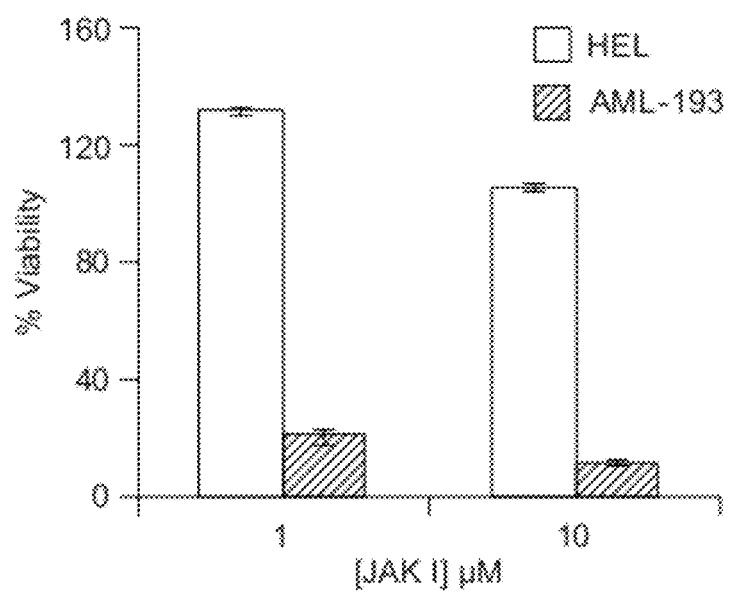
Figure 6B:
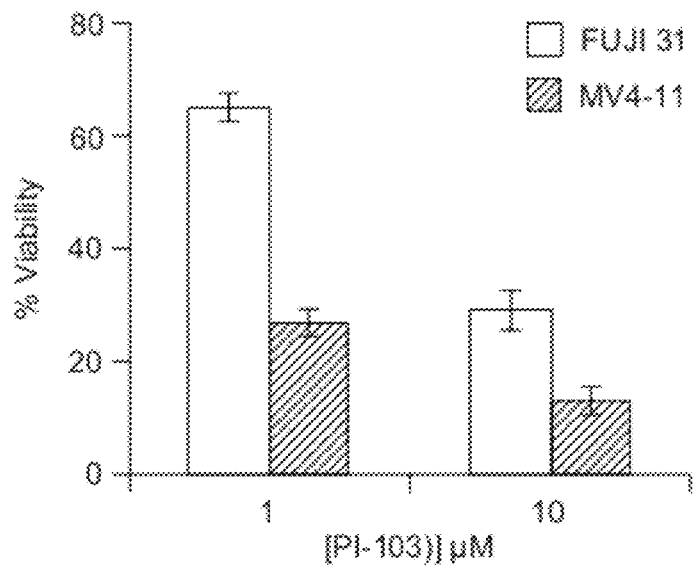
Figure 6C:
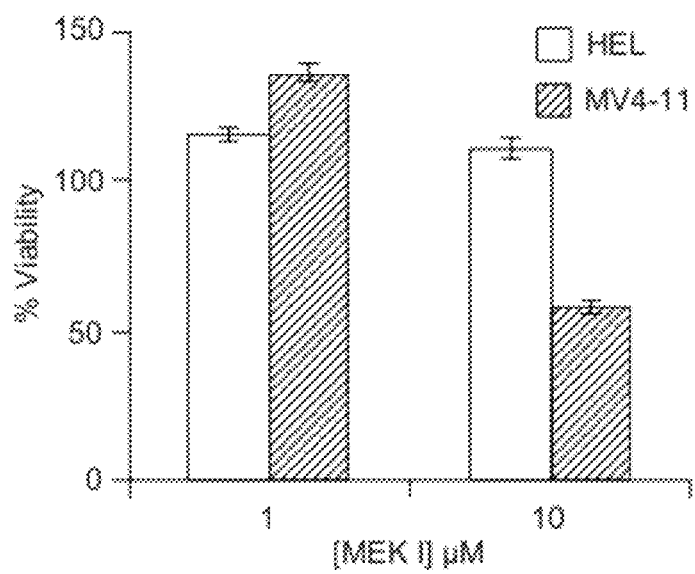
Figure 6D:
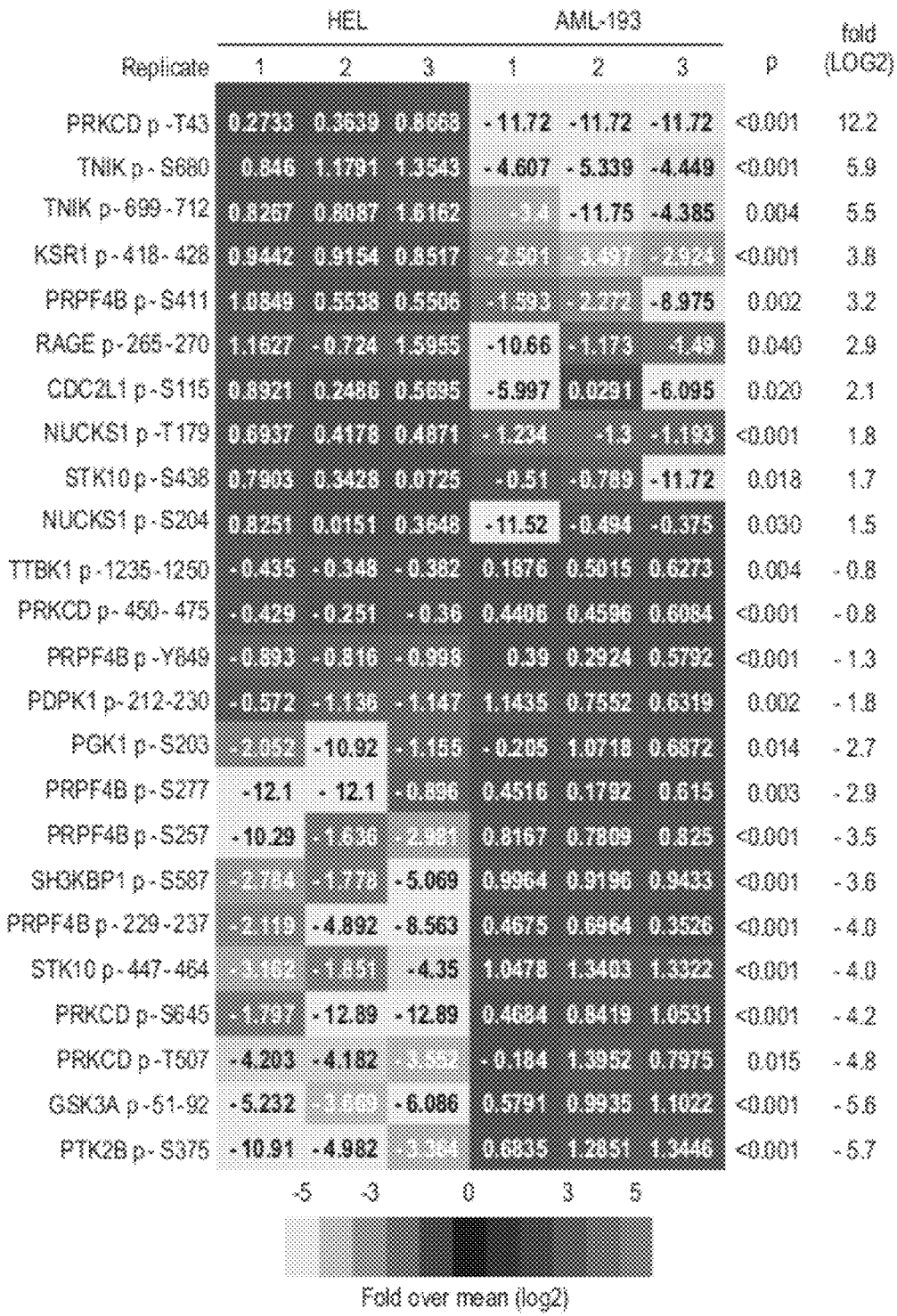
Figure 6E:
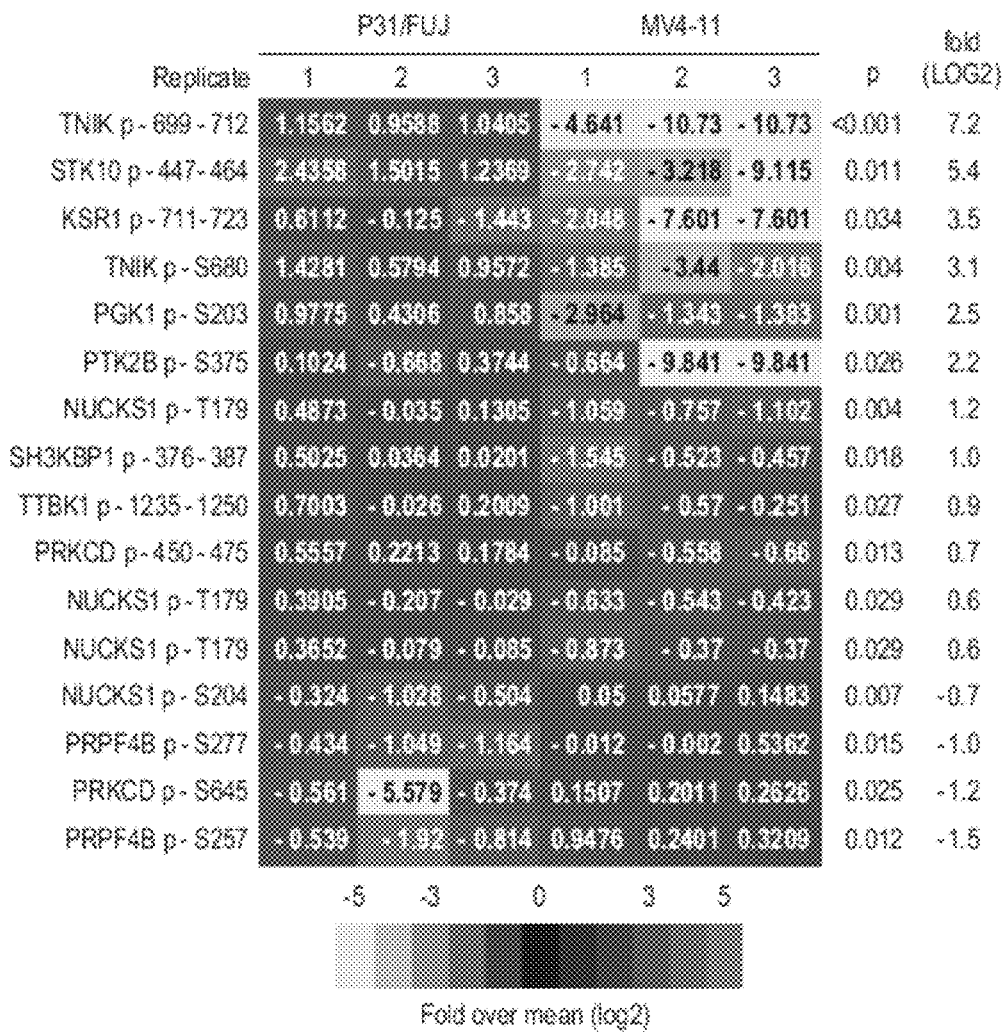
Figure 6F:
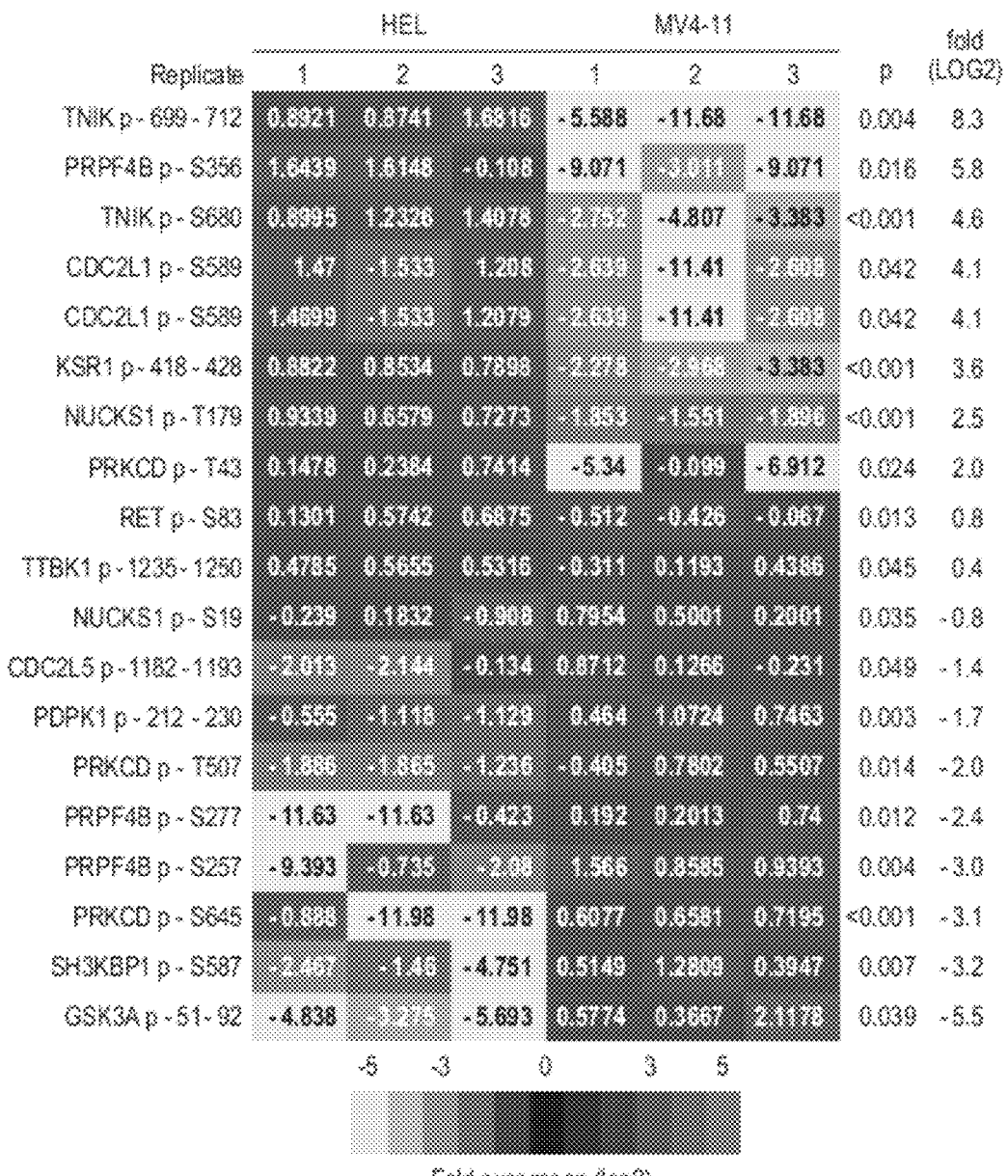

The TIQUAS approach was then used to compare basal phosphorylation levels in HEL versus AML-193 (resistant and sensitive to JAK I), P31/FUJ versus MV4-11 (resistant and sensitive to PI-103), and HEL versus MV4-11 (resistant and sensitive to MEK I); these experiments were performed in triplicate (FIGS. 6A, B and C). More than 3000 phosphopeptides were identified in these analyses. A total of 1095 phosphopeptides were quantified across these cell lines, from which hundreds showed significant ($p<0.05$) and robust (>2 fold) differences between the sensitive and resistant cell lines (Examples of these are shown in FIGS. 6D, E and F).

Materials and Methods

Cell Culture.

Acute myeloid leukemia cell lines (AML-193, CMK, CTS, HEL, Kasumi-1, KG-1, MV4-11 and P31/FUJ) and murine NIH/3T3 fibroblasts were routinely cultured at 37° C. in a humidified atmosphere of 5% $CO_2$ in medium supplemented with 10% bovine serum, 100 units/ml penicillin, 100 µg/ml streptomycin. AML cell lines were maintained at about 5 to $10\times10^5$ cell/ml in RPMI with an additional supplement of 50 µM beta-mercaptoethanol. NIH-3T3 fibroblasts were grown in DMEM medium.

For phosphoproteomic studies, AML cells were seeded at $5\times10^5$ cells/ml in fresh medium the day before the experiment. Each culture contained $5\times10^6$ cells in 10 ml and was performed in three independent cell cultures. When testing the effect of drug inhibitors, the cells were treated with 1 µM PI-103, 500 nM MEK I inhibitor and 500 nM JAK I inhibitor (528100, 444937 and 420099 from Calbiochem, respectively) for 1 hour prior to cell harvesting.

Cells were harvested by centrifugation at 300×g for 10 min, and washed twice with ice cold PBS containing 1 mM sodium vanadate and 1 mM sodium fluoride. Lysis was performed using a denaturing buffer (20 mM HEPES pH 8.0, 8 M urea, 1 mM sodium vanadate, 1 mM sodium fluoride, 2.5 mM sodium pyrophosphate, 1 mM β-glycerol-phosphate) at a concentration of $10\times10^6$ cells/ml. Further protein solubilization was achieved by sonication. Lysate debris was cleared by centrifugation at 20000×g for 10 min and protein concentration of the supernatants was determined by Bradford assay. Samples were then kept frozen at −80° C. until further analysis.

Sensitivity of AML cell lines to drug treatment. Eight cell lines (AML-193, CMK, CTS, HEL, Kasumi-1, KG-1, MV4-11 and P31/FUJ) were seeded in 96 well plates at $1\times10^5$ cell/ml in triplicate for each condition. After a recovery period of 2 h, cells were treated with increasing concentrations (1 nM, 10 nM, 100 nM, 1 µM and 10 µM) of FLT3 inhibitor, MEK I inhibitor, JAK I inhibitor, LY294002, PI-103 and IC87114. As controls, cells were both treated with the vehicle (DMSO) and left untreated. After 72 hours treatment, cell viability was assessed by MTS assay (CellTiter 96® AQueous One Solution Cell Proliferation assay, Promega Corporation, Madison, Wis., USA).

Digestion and Solid Phase Extraction.

Sample reduction and alkylation were performed with 4.1 mM DTT and 8.3 mM iodoacetamide in the dark and at room temperature for 15 min each. After diluting the samples to 2 M urea with HEPES pH 8.0, trypsinization was performed using 10 TAME units of immobilised TLCK-trypsin per $5\times10^6$ cells for 16 h at 37° C. Digestion was stopped by adding TFA at a final concentration of 1%. The resultant peptide solutions were desalted using Sep-Pak $C_{18}$ columns (Waters UK Ltd, Manchester, UK) according to manufacturer guidelines. Peptide elution was carried out with 5 ml 50% ACN/0.1% TFA.

Immobilized Metal Ion Affinity Chromatography (IMAC).

Phosphopeptide separation was achieved using an adapted IMAC enrichment protocol (Alcolea, M. P. et al., *J Proteome Res* 8 (8), 3808 (2009)). In short, each sample was incubated for 30 min at room temperature with 300 µl of Fe(III)-coated sepharose high performance beads used as a 50% slurry in 50% ACN/0.1% TFA. Unbound peptides were discarded and beads washed with 300 µl of 50% ACN/0.1% TFA twice. The enriched phosphopeptide fraction was eluted with 300 µl ammonia water 1.5%, pH 11. A second elution using 50 µl ammonia water 1.5%, pH 11 containing 50% ACN allowed further enrichment. Eluted peptides were finally dried in a SpeedVac and stored at −80° C.

Nanoflow-Liquid Chromatography Tandem Mass Spectrometry (LC-MS/MS).

For phosphoproteomic experiments, dried phosphopeptide enriched samples were dissolved in 10 µl of 0.1% TFA and analysed in a LC-MS/MS system. The latter consisted of an LTQ-Orbitrap XL mass spectrometer (Thermo Fisher Scientific, Hemel Hempstead, UK) connected online to a nanoflow ultra-high pressure liquid chromatography (nanoAcquity, Waters/Micromass) that delivered a flow rate of 5 μL/min (loading) and 400 nL/min (elution) with an operating back pressure of about 3,000 psi. Separations were performed in a BEH 100 μm×100 mm column (Waters/Micromass) The mobile phases were solution A, 0.1% FA in LC-MS grade water, and solution B, 0.1% FA in LC-MS grade ACN. Gradient runs were from 1% B to 35% B in 100 min followed by a 5 min wash at 85% B and a 7 min equilibration step at 1% B. Full scan survey spectra (m/z 350-1600) were acquired in the LTQ-Orbitrap XL with a resolution of 60000 at m/z 400. A data dependent analysis (DDA) was employed in which the 5 most abundant multiply charged ions present in the survey spectrum were automatically mass-selected and fragmented by collision-induced dissociation (normalized collision energy 35%). MS scans were followed by 5 MS/MS scans (m/z 50-2000). Dynamic exclusion was enabled with the exclusion list restricted to 500 entries, exclusion duration of 40 seconds and mass window of 10 ppm.

Data Analysis.

LTQ-Orbitrap MS/MS data were smoothed and centroided using Mascot Distiller. The processed files were searched against the human or mouse sequence library in the international protein index (IPI Mouse v3.49, 165169 sequences and IPI Human. v3.56, 76539 sequences) using the Mascot search engine. Searches were automated with Mascot Daemon (v2.2.2; Matrix Science, London, UK). The parameters included, choosing trypsin as digestion enzyme with one missed cleavage allowed, carbamidomethyl (C) was set as fixed modification, and Pyro-glu (N-term), Oxidation (M) and Phospho (STY) were variable modifications. Datasets were searched with a mass tolerance of ±7 ppm and a fragment mass tolerance of ±800 mmu. Hits were considered significant when they were above the statistical significant threshold (Expectation value <0.05) (as returned by Mascot). False positive rate as estimated by searches against a decoy database was about 2%. Sites of modification are reported when these were returned by Mascot and were also present in the phosphoELM database. Otherwise the site of modification was deemed to be ambiguous; in such cases phosphopeptides are reported as the start-end residues within the protein sequence.

Phosphopeptides identified by Mascot with a statistical significant threshold were placed in a database of peptides quantifiable by LC-MS. The computer programme PESCAL, as described herein (Cutillas, P. R. & Vanhaesebroeck, B. Quantitative profile of five murine core proteomes using label-free functional proteomics. *Mol Cell Proteomics* 6, 1560-1573 (2007)) was then used. PESCAL quantifies the intensities of the peptides present in the database across all the samples one wishes to compare. PESCAL uses the m/z and retention time of the selected peptides to construct extracted ion chromatograms (XICs) for the first three isotopes of each ion. This applies restrictions on the molecular mass, retention time and charge, which permits the unequivocal identification of the LC-MS elution profiles corresponding to the studied phosphopeptides. Windows for XIC construction were 7 ppm and 5 min for m/z and retention time, respectively. The intensity values could then be calculated by determining the peak height of each individual XIC.

The invention claimed is:

1. A label-free method for quantifying post-translational protein modifications in a plurality of samples, each sample containing a mixture of proteins obtained from a biological sample, the method comprising:
   (a) obtaining peptides from the mixture of proteins in each sample of the plurality of samples by a process comprising cleaving the mixture of proteins in each sample into peptides using a protease to obtain a plurality of peptide samples;
   (b) enriching post-translationally modified peptides from each sample to obtain a plurality of enriched peptide samples, each sample being enriched for post-translationally modified peptides;
   (c) carrying out liquid chromatography-mass spectrometry (LC-MS) on the plurality of enriched peptide samples and obtaining MS data for the peptides in each sample of the plurality of samples, said MS data including mass to charge (m/z) ratio, charge (z), and relative retention time;
   (d) comparing the MS data obtained in step (c) to a known reference database in order to identify the post-translationally modified peptides;
   (e) compiling a database consisting of the MS data for all peptides across the plurality of enriched post-translationally modified peptide samples;
   (f) constructing extracted ion chromatograms (XICs) for each post-translationally modified peptide present in the database compiled in step (e) across the plurality of enriched peptide samples; and
   (g) quantifying each post-translationally modified peptide in the database across the plurality of enriched peptide samples by determining the peak height or area of each XIC, thereby quantifying post-translational protein modifications in the plurality of samples containing mixtures of proteins.

2. The method of claim 1, wherein the modified peptides are phosphorylated peptides.

3. The method of claim 1, wherein the protease is selected from the group consisting of trypsin, chymotrypsin, Arg-C, pepsin, V8, Lys-C, Asp-C and AspN.

4. The method of claim 1, wherein the step of cleaving the proteins into peptides comprises cleaving said proteins into peptides of 5 to 30 amino acids.

5. The method of claim 1, wherein the step of enriching modified peptides is carried out using chromatography.

6. The method of claim 5, wherein the chromatography is selected from the group consisting of immobilized metal ion affinity chromatography (IMAC), titanium dioxide ($TiO_2$) chromatography and zirconium dioxide ($ZrO_2$) chromatography.

7. The method of claim 1, wherein the step of enriching post-translationally modified peptides is carried out using antibody-based methods.

8. The method of claim 1, wherein said LC-MS is liquid-chromatography tandem mass spectrometry (LC-MS/MS).

9. The method of claim 1, wherein the enriching step is carried out using multidimensional chromatography.

10. The method of claim 9, wherein the multidimensional chromatography is carried out using strong cation exchange high performance liquid chromatography (SCX-HPLC), immobilized metal ion affinity chromatography (IMAC) and titanium dioxide ($TiO_2$) chromatography.

11. The method of claim 9, wherein the multidimensional chromatography is carried out using anion exchange high performance liquid chromatography (SAX-HPLC), immobilized metal ion affinity chromatography (IMAC) and titanium dioxide ($TiO_2$) chromatography.

12. The method of claim 1, wherein the biological sample is obtained from a bodily fluid, tissue, or cell line.

* * * * *

SEQUENCE LISTING

```
<160> NUMBER OF SEQ ID NOS: 94

<210> SEQ ID NO 1
<211> LENGTH: 20
<212> TYPE: PRT
<213> ORGANISM: Artificial
<220> FEATURE:
<223> OTHER INFORMATION: mitogen-activated protein kinase 3 (pERK1)
      peptide
<220> FEATURE:
<221> NAME/KEY: PHOSPHORYLATION
<222> LOCATION: (16)..(16)
<223> OTHER INFORMATION: Phosphotyrosine or phosphorylated tyrosine

<400> SEQUENCE: 1

Ile Ala Asp Pro Glu His Asp His Thr Gly Phe Leu Thr Glu Pro Tyr
1               5                   10                  15

Val Ala Thr Arg
            20

<210> SEQ ID NO 2
<211> LENGTH: 14
<212> TYPE: PRT
<213> ORGANISM: Artificial
<220> FEATURE:
<223> OTHER INFORMATION: 27 kDa protein

<400> SEQUENCE: 2

Val Val Ala Ala Ala Leu Ser Ser Pro Val Glu Ala Ala Lys
1               5                   10

<210> SEQ ID NO 3
<211> LENGTH: 9
```

```
<212> TYPE: PRT
<213> ORGANISM: Artificial
<220> FEATURE:
<223> OTHER INFORMATION: Protein phosphatase 1 regulatory subunit 11

<400> SEQUENCE: 3

Cys Cys Cys Ile Tyr Glu Lys Pro Arg
1               5

<210> SEQ ID NO 4
<211> LENGTH: 12
<212> TYPE: PRT
<213> ORGANISM: Artificial
<220> FEATURE:
<223> OTHER INFORMATION: Adult male corpora quadrigemina cDNA, RIKEN
      full-length enriched library, clone:B230341L19 product:
      hypothetical RhoGAP domain/Pleckstrin homology (PH) domain
      containing protein, full insert sequence

<400> SEQUENCE: 4

Gly Glu Pro Gly Ser Pro Gly Leu Pro Thr His Arg
1               5                   10

<210> SEQ ID NO 5
<211> LENGTH: 12
<212> TYPE: PRT
<213> ORGANISM: Artificial
<220> FEATURE:
<223> OTHER INFORMATION: Isoform 1 of Vacuolar protein sorting-
      associated protein 26B

<400> SEQUENCE: 5

Ser Met Ser His Gln Ala Ala Ile Ala Ser Gln Arg
1               5                   10

<210> SEQ ID NO 6
<211> LENGTH: 15
<212> TYPE: PRT
<213> ORGANISM: Artificial
<220> FEATURE:
<223> OTHER INFORMATION: carbamoyl-phosphate synthetase 2, aspartate
      transcarbamylase, and dihydroorotase

<400> SEQUENCE: 6

Ile His Arg Ala Ser Asp Pro Gly Leu Pro Ala Glu Glu Pro Lys
1               5                   10                  15

<210> SEQ ID NO 7
<211> LENGTH: 12
<212> TYPE: PRT
<213> ORGANISM: Artificial
<220> FEATURE:
<223> OTHER INFORMATION: Fos-related antigen 2

<400> SEQUENCE: 7

Arg Ser Pro Pro Thr Ser Gly Leu Gln Ser Leu Arg
1               5                   10

<210> SEQ ID NO 8
<211> LENGTH: 13
<212> TYPE: PRT
<213> ORGANISM: Artificial
<220> FEATURE:
<223> OTHER INFORMATION: histocompatibility 2, M region locus 3

<400> SEQUENCE: 8

Ser Arg Leu Glu Ser Ala Gly Thr Ala Glu Tyr Phe Arg
1               5                   10
```

```
<210> SEQ ID NO 9
<211> LENGTH: 24
<212> TYPE: PRT
<213> ORGANISM: Artificial
<220> FEATURE:
<223> OTHER INFORMATION: Isoform 1 of Reticulon-4;

<400> SEQUENCE: 9

Thr Ser Asn Pro Phe Leu Val Ala Ile His Asp Ser Glu Ala Asp Tyr
1               5                   10                  15

Val Thr Thr Asp Asn Leu Ser Lys
            20

<210> SEQ ID NO 10
<211> LENGTH: 18
<212> TYPE: PRT
<213> ORGANISM: Artificial
<220> FEATURE:
<223> OTHER INFORMATION: CLASP1 isoform 14

<400> SEQUENCE: 10

Ser Ser Ser Pro Gly Lys Leu Leu Gly Ser Gly Leu Ala Gly Gly Ser
1               5                   10                  15

Ser Arg

<210> SEQ ID NO 11
<211> LENGTH: 16
<212> TYPE: PRT
<213> ORGANISM: Artificial
<220> FEATURE:
<223> OTHER INFORMATION: Adult male testis cDNA, RIKEN full-length
      enriched library, clone:4922505F07 product:ATP citrate lyase, full
      insert sequence

<400> SEQUENCE: 11

Thr Ala Ser Phe Ser Glu Ser Arg Ala Asp Glu Val Ala Pro Ala Lys
1               5                   10                  15

<210> SEQ ID NO 12
<211> LENGTH: 20
<212> TYPE: PRT
<213> ORGANISM: Artificial
<220> FEATURE:
<223> OTHER INFORMATION: Mitogen-activated protein kinase kinase kinase
      3

<400> SEQUENCE: 12

Ile Lys Pro Ser Gln Ser Ala Gly Asp Ile Asn Thr Ile Tyr Gln Ala
1               5                   10                  15

Pro Glu Pro Arg
            20

<210> SEQ ID NO 13
<211> LENGTH: 18
<212> TYPE: PRT
<213> ORGANISM: Artificial
<220> FEATURE:
<223> OTHER INFORMATION: melanoma inhibitory activity 3

<400> SEQUENCE: 13

Ser Ser Ser Pro Ala Lys Ala Val Asp Glu Gly Lys Val Asn Met Ala
1               5                   10                  15

Pro Lys
```

```
<210> SEQ ID NO 14
<211> LENGTH: 18
<212> TYPE: PRT
<213> ORGANISM: Artificial
<220> FEATURE:
<223> OTHER INFORMATION: Isoform Alpha of Paxillin

<400> SEQUENCE: 14

Tyr Ala His Gln Gln Pro Pro Ser Pro Leu Pro Val Tyr Ser Ser Ser
1               5                   10                  15

Ala Lys

<210> SEQ ID NO 15
<211> LENGTH: 27
<212> TYPE: PRT
<213> ORGANISM: Artificial
<220> FEATURE:
<223> OTHER INFORMATION: Isoform 1 of ADP-ribosylation factor-binding
      protein GGA2

<400> SEQUENCE: 15

Leu Ala Ser Asp Thr Thr Asp Asp Asp Ala Leu Ala Glu Ile Leu
1               5                   10                  15

Gln Ala Asn Asp Leu Leu Thr Gln Gly Val Arg
            20                  25

<210> SEQ ID NO 16
<211> LENGTH: 12
<212> TYPE: PRT
<213> ORGANISM: Artificial
<220> FEATURE:
<223> OTHER INFORMATION: BTB/POZ domain-containing protein KCTD10

<400> SEQUENCE: 16

Thr Thr Ser Phe Lys Gly Ala Ser Pro Ser Ser Lys
1               5                   10

<210> SEQ ID NO 17
<211> LENGTH: 24
<212> TYPE: PRT
<213> ORGANISM: Artificial
<220> FEATURE:
<223> OTHER INFORMATION: Pinin

<400> SEQUENCE: 17

Glu Gly Glu Lys Gln Gln Asp Ser Gln Pro Glu Glu Val Met Asp Val
1               5                   10                  15

Leu Glu Met Val Glu Ser Val Lys
            20

<210> SEQ ID NO 18
<211> LENGTH: 15
<212> TYPE: PRT
<213> ORGANISM: Artificial
<220> FEATURE:
<223> OTHER INFORMATION: Isoform 1 of Protein FAM62B

<400> SEQUENCE: 18

Ser Ser Ser Ser Leu Leu Ala Ser Pro Ser His Ile Ala Ala Lys
1               5                   10                  15

<210> SEQ ID NO 19
<211> LENGTH: 18
<212> TYPE: PRT
<213> ORGANISM: Artificial
```

```
<220> FEATURE:
<223> OTHER INFORMATION: Tight junction protein ZO-2

<400> SEQUENCE: 19

Val Phe Leu Arg Pro Ser Pro Glu Asp Glu Ala Ile Tyr Gly Pro Asn
1               5                   10                  15

Thr Lys

<210> SEQ ID NO 20
<211> LENGTH: 15
<212> TYPE: PRT
<213> ORGANISM: Artificial
<220> FEATURE:
<223> OTHER INFORMATION: Forkhead box protein K1

<400> SEQUENCE: 20

Ser Ala Pro Ala Ser Pro Thr His Pro Gly Leu Met Ser Pro Arg
1               5                   10                  15

<210> SEQ ID NO 21
<211> LENGTH: 15
<212> TYPE: PRT
<213> ORGANISM: Artificial
<220> FEATURE:
<223> OTHER INFORMATION: 66 kDa protein

<400> SEQUENCE: 21

Ser Ala Pro Ala Ser Pro Thr His Pro Gly Leu Met Ser Pro Arg
1               5                   10                  15

<210> SEQ ID NO 22
<211> LENGTH: 15
<212> TYPE: PRT
<213> ORGANISM: Artificial
<220> FEATURE:
<223> OTHER INFORMATION: similar to interferon regulatory factor 2
      binding protein 2 isoform 1

<400> SEQUENCE: 22

Arg Lys Pro Ser Pro Glu Pro Glu Gly Glu Val Gly Pro Pro Lys
1               5                   10                  15

<210> SEQ ID NO 23
<211> LENGTH: 21
<212> TYPE: PRT
<213> ORGANISM: Artificial
<220> FEATURE:
<223> OTHER INFORMATION: Isoform 2 of Epidermal growth factor receptor
      substrate 15-like 1

<400> SEQUENCE: 23

Thr Val Phe Ala Gly Ala Val Pro Val Leu Pro Ala Ser Pro Pro Pro
1               5                   10                  15

Lys Asp Ser Leu Arg
            20

<210> SEQ ID NO 24
<211> LENGTH: 13
<212> TYPE: PRT
<213> ORGANISM: Artificial
<220> FEATURE:
<223> OTHER INFORMATION: CD2-associated protein

<400> SEQUENCE: 24

Phe Asn Gly Gly His Ser Pro Thr Gln Ser Pro Glu Lys
1               5                   10
```

<210> SEQ ID NO 25
<211> LENGTH: 24
<212> TYPE: PRT
<213> ORGANISM: Artificial
<220> FEATURE:
<223> OTHER INFORMATION: Isoform 1 of Eukaryotic translation initiation
      factor 4 gamma 1

<400> SEQUENCE: 25

Ile Thr Lys Pro Gly Ser Ile Asp Ser Asn Asn Gln Leu Phe Ala Pro
1               5                   10                  15

Gly Gly Arg Leu Ser Trp Gly Lys
            20

<210> SEQ ID NO 26
<211> LENGTH: 12
<212> TYPE: PRT
<213> ORGANISM: Artificial
<220> FEATURE:
<223> OTHER INFORMATION: Neural Wiskott-Aldrich syndrome protein;

<400> SEQUENCE: 26

Glu Thr Ser Lys Val Ile Tyr Asp Phe Ile Glu Lys
1               5                   10

<210> SEQ ID NO 27
<211> LENGTH: 13
<212> TYPE: PRT
<213> ORGANISM: Artificial
<220> FEATURE:
<223> OTHER INFORMATION: Isoform 1 of U1 small nuclear ribonucleoprotein
      70 kDa

<400> SEQUENCE: 27

Tyr Asp Glu Arg Pro Gly Pro Ser Pro Leu Pro His Arg
1               5                   10

<210> SEQ ID NO 28
<211> LENGTH: 19
<212> TYPE: PRT
<213> ORGANISM: Artificial
<220> FEATURE:
<223> OTHER INFORMATION: Protein LYRIC

<400> SEQUENCE: 28

Lys Arg Glu Glu Ala Ala Pro Pro Thr Pro Ala Pro Asp Asp Leu Ala
1               5                   10                  15

Gln Leu Lys

<210> SEQ ID NO 29
<211> LENGTH: 8
<212> TYPE: PRT
<213> ORGANISM: Artificial
<220> FEATURE:
<223> OTHER INFORMATION: Myristoylated alanine-rich C-kinase substrate

<400> SEQUENCE: 29

Leu Ser Gly Phe Ser Phe Lys Lys
1               5

<210> SEQ ID NO 30
<211> LENGTH: 32
<212> TYPE: PRT
<213> ORGANISM: Artificial
<220> FEATURE:

```
<223> OTHER INFORMATION: Isoform 2 of Epidermal growth factor receptor
      substrate 15-like 1

<400> SEQUENCE: 30

Ser Leu Glu Gln Tyr Asp Gln Val Pro Asp Gly Val Ser Gly Thr Ser
1               5                   10                  15

Leu Pro Asp Leu Ala Thr Leu Asn Glu Gly Ile Leu Leu Ala Glu Arg
            20                  25                  30

<210> SEQ ID NO 31
<211> LENGTH: 14
<212> TYPE: PRT
<213> ORGANISM: Artificial
<220> FEATURE:
<223> OTHER INFORMATION: Isoform 1 of Leucine-rich repeat flightless-
      interacting protein 1

<400> SEQUENCE: 31

Ser Glu Gln Gln Ala Glu Ala Leu Asp Ser Pro Gln Lys Lys
1               5                   10

<210> SEQ ID NO 32
<211> LENGTH: 19
<212> TYPE: PRT
<213> ORGANISM: Artificial
<220> FEATURE:
<223> OTHER INFORMATION: Isoform 1 of Nuclear-interacting partner of ALK

<400> SEQUENCE: 32

Ser Met Gly Thr Gly Asp Ser Ala Gly Val Glu Val Pro Ser Ser Pro
1               5                   10                  15

Leu Arg Arg

<210> SEQ ID NO 33
<211> LENGTH: 19
<212> TYPE: PRT
<213> ORGANISM: Artificial
<220> FEATURE:
<223> OTHER INFORMATION: Isoform 1 of Nuclear-interacting partner of ALK

<400> SEQUENCE: 33

Ser Met Gly Thr Gly Asp Ser Ala Gly Val Glu Val Pro Ser Ser Pro
1               5                   10                  15

Leu Arg Arg

<210> SEQ ID NO 34
<211> LENGTH: 16
<212> TYPE: PRT
<213> ORGANISM: Artificial
<220> FEATURE:
<223> OTHER INFORMATION: similar to la related protein isoform 1

<400> SEQUENCE: 34

Ala Val Thr Pro Val Pro Thr Lys Thr Glu Glu Val Ser Asn Leu Lys
1               5                   10                  15

<210> SEQ ID NO 35
<211> LENGTH: 16
<212> TYPE: PRT
<213> ORGANISM: Artificial
<220> FEATURE:
<223> OTHER INFORMATION: WAS/WASL interacting protein family member 1

<400> SEQUENCE: 35

Asn Leu Ser Leu Thr Ser Ser Ala Pro Pro Leu Pro Ser Pro Gly Arg
```

<210> SEQ ID NO 36
<211> LENGTH: 15
<212> TYPE: PRT
<213> ORGANISM: Artificial
<220> FEATURE:
<223> OTHER INFORMATION: Isoform 1 of Lipin-2

<400> SEQUENCE: 36

Ser Asp Ser Glu Leu Glu Val Lys Pro Ser Glu Ser Leu Leu Arg
1               5                   10                  15

<210> SEQ ID NO 37
<211> LENGTH: 10
<212> TYPE: PRT
<213> ORGANISM: Artificial
<220> FEATURE:
<223> OTHER INFORMATION: Serpin B13

<400> SEQUENCE: 37

Ile Lys Ser Glu Glu Glu Glu Ile Glu Lys
1               5                   10

<210> SEQ ID NO 38
<211> LENGTH: 26
<212> TYPE: PRT
<213> ORGANISM: Artificial
<220> FEATURE:
<223> OTHER INFORMATION: mRNA decapping enzyme 1A

<400> SEQUENCE: 38

Gln Lys Ser Pro Leu Leu Asn Gln Pro Val Pro Glu Leu Ser His Ser
1               5                   10                  15

Ser Leu Val Ala Ser Gln Ser Pro Phe Arg
            20                  25

<210> SEQ ID NO 39
<211> LENGTH: 10
<212> TYPE: PRT
<213> ORGANISM: Artificial
<220> FEATURE:
<223> OTHER INFORMATION: Microtubule-associated protein 1 A

<400> SEQUENCE: 39

Gly Glu Lys Glu Leu Ser Ser Glu Pro Arg
1               5                   10

<210> SEQ ID NO 40
<211> LENGTH: 33
<212> TYPE: PRT
<213> ORGANISM: Artificial
<220> FEATURE:
<223> OTHER INFORMATION: Isoform 4 of Heterogeneous nuclear
      ribonucleoproteins C1/C2

<400> SEQUENCE: 40

Met Glu Ser Glu Ala Gly Ala Asp Asp Ser Ala Glu Glu Gly Asp Leu
1               5                   10                  15

Leu Asp Asp Asp Asp Asn Glu Asp Arg Gly Asp Asp Gln Leu Glu Leu
            20                  25                  30

Lys

<210> SEQ ID NO 41
<211> LENGTH: 22

<212> TYPE: PRT
<213> ORGANISM: Artificial
<220> FEATURE:
<223> OTHER INFORMATION: Isoform 1 of Rho guanine nucleotide exchange
      factor 10

<400> SEQUENCE: 41

Asn Asp Leu Ser Ser Ser Ser Gly Ser Leu Asn Leu Ser His Gly Ser
1               5                   10                  15

Ser Ser Leu Glu His Arg
            20

<210> SEQ ID NO 42
<211> LENGTH: 32
<212> TYPE: PRT
<213> ORGANISM: Artificial
<220> FEATURE:
<223> OTHER INFORMATION: Eukaryotic translation initiation factor 4E-
      binding protein 1

<400> SEQUENCE: 42

Arg Val Ala Leu Gly Asp Gly Val Gln Leu Pro Pro Gly Asp Tyr Ser
1               5                   10                  15

Thr Thr Pro Gly Gly Thr Leu Phe Ser Thr Thr Pro Gly Gly Thr Arg
            20                  25                  30

<210> SEQ ID NO 43
<211> LENGTH: 46
<212> TYPE: PRT
<213> ORGANISM: Artificial
<220> FEATURE:
<223> OTHER INFORMATION: Isoform 1 of Ataxin-2-like protein

<400> SEQUENCE: 43

Ser Ala Ala Pro Ala Pro Val Ser Ala Ser Cys Pro Glu Pro Pro Ile
1               5                   10                  15

Gly Ser Ala Val Ala Ser Ser Ala Ser Ile Pro Val Thr Ser Ser Val
            20                  25                  30

Val Asp Pro Gly Ala Gly Ser Ile Ser Pro Ala Ser Pro Lys
        35                  40                  45

<210> SEQ ID NO 44
<211> LENGTH: 17
<212> TYPE: PRT
<213> ORGANISM: Artificial
<220> FEATURE:
<223> OTHER INFORMATION: MKL/myocardin-like protein 2

<400> SEQUENCE: 44

Ser Gly Glu Ile Ser Phe Pro Ile Lys Glu Glu Pro Ser Pro Ile Ser
1               5                   10                  15

Lys

<210> SEQ ID NO 45
<211> LENGTH: 14
<212> TYPE: PRT
<213> ORGANISM: Artificial
<220> FEATURE:
<223> OTHER INFORMATION: Vimentin

<400> SEQUENCE: 45

Thr Tyr Ser Leu Gly Ser Ala Leu Arg Pro Ser Thr Ser Arg
1               5                   10

```
<210> SEQ ID NO 46
<211> LENGTH: 26
<212> TYPE: PRT
<213> ORGANISM: Artificial
<220> FEATURE:
<223> OTHER INFORMATION: mRNA decapping enzyme 1A

<400> SEQUENCE: 46

Gln Lys Ser Pro Leu Leu Asn Gln Pro Val Pro Glu Leu Ser His Ser
1               5                   10                  15

Ser Leu Val Ala Ser Gln Ser Pro Phe Arg
            20                  25

<210> SEQ ID NO 47
<211> LENGTH: 11
<212> TYPE: PRT
<213> ORGANISM: Artificial
<220> FEATURE:
<223> OTHER INFORMATION: Protein FAM122A

<400> SEQUENCE: 47

His Gly Leu Leu Leu Pro Ala Ser Pro Val Arg
1               5                   10

<210> SEQ ID NO 48
<211> LENGTH: 8
<212> TYPE: PRT
<213> ORGANISM: Artificial
<220> FEATURE:
<223> OTHER INFORMATION: Isoform A of Drebrin

<400> SEQUENCE: 48

Leu Ser Ser Pro Val Leu His Arg
1               5

<210> SEQ ID NO 49
<211> LENGTH: 14
<212> TYPE: PRT
<213> ORGANISM: Artificial
<220> FEATURE:
<223> OTHER INFORMATION: Nucleolar protein Nop56

<400> SEQUENCE: 49

Lys Phe Ser Glu Glu Pro Glu Val Ala Ala Asn Phe Thr Lys
1               5                   10

<210> SEQ ID NO 50
<211> LENGTH: 12
<212> TYPE: PRT
<213> ORGANISM: Artificial
<220> FEATURE:
<223> OTHER INFORMATION: 0 day neonate eyeball cDNA, RIKEN full-length
      enriched library, clone:E130120C15 product:CDNA FLJ31417 FIS,
      CLONE NT2NE2000327, WEAKLY SIMILAR TO GLUCOAMYLASE S1/S2
      (EC 3.2.1.3) homolog

<400> SEQUENCE: 50

Val Val Pro Gln Gln Ile Thr His Thr Ser Pro Arg
1               5                   10

<210> SEQ ID NO 51
<211> LENGTH: 20
<212> TYPE: PRT
<213> ORGANISM: Artificial
<220> FEATURE:
<223> OTHER INFORMATION: Mitogen-activated protein kinase kinase kinase
      3;
```

-continued

```
<400> SEQUENCE: 51

Ile Lys Pro Ser Gln Ser Ala Gly Asp Ile Asn Thr Ile Tyr Gln Ala
1               5                   10                  15

Pro Glu Pro Arg
            20

<210> SEQ ID NO 52
<211> LENGTH: 16
<212> TYPE: PRT
<213> ORGANISM: Artificial
<220> FEATURE:
<223> OTHER INFORMATION: Serine/threonine-protein kinase LATS2

<400> SEQUENCE: 52

Met Arg Pro Lys Thr Phe Pro Ala Thr Thr Tyr Ser Gly Asn Ser Arg
1               5                   10                  15

<210> SEQ ID NO 53
<211> LENGTH: 16
<212> TYPE: PRT
<213> ORGANISM: Artificial
<220> FEATURE:
<223> OTHER INFORMATION: Serine/threonine-protein kinase PRP4 homolog

<400> SEQUENCE: 53

Glu Val Ile Glu Ala Ser Asp Lys Glu Gly Leu Ser Pro Ala Lys Arg
1               5                   10                  15

<210> SEQ ID NO 54
<211> LENGTH: 19
<212> TYPE: PRT
<213> ORGANISM: Artificial
<220> FEATURE:
<223> OTHER INFORMATION: Mitogen-activated protein kinase 3

<400> SEQUENCE: 54

Ile Ala Asp Pro Glu His Asp His Thr Gly Phe Leu Thr Glu Tyr Val
1               5                   10                  15

Ala Thr Arg

<210> SEQ ID NO 55
<211> LENGTH: 12
<212> TYPE: PRT
<213> ORGANISM: Artificial
<220> FEATURE:
<223> OTHER INFORMATION: Elongation factor 2 kinase

<400> SEQUENCE: 55

Thr Leu Ser Ser Ser Arg Pro Pro Leu Leu Leu Arg
1               5                   10

<210> SEQ ID NO 56
<211> LENGTH: 14
<212> TYPE: PRT
<213> ORGANISM: Artificial
<220> FEATURE:
<223> OTHER INFORMATION: Isoform 1 of Serine/threonine-protein kinase
      N2;

<400> SEQUENCE: 56

Ser Lys Ser Glu Tyr Glu Leu Ser Ile Pro Asp Ser Gly Arg
1               5                   10

<210> SEQ ID NO 57
<211> LENGTH: 16
```

```
<212> TYPE: PRT
<213> ORGANISM: Artificial
<220> FEATURE:
<223> OTHER INFORMATION: Serine/threonine-protein kinase PFTAIRE-1;

<400> SEQUENCE: 57

Thr Gln Ser Thr Phe Asp Pro Phe Glu Lys Pro Ala Asn Gln Val Lys
1               5                   10                  15

<210> SEQ ID NO 58
<211> LENGTH: 14
<212> TYPE: PRT
<213> ORGANISM: Artificial
<220> FEATURE:
<223> OTHER INFORMATION: Tyrosine-protein kinase-protein kinase SgK269;

<400> SEQUENCE: 58

Ser Ala Pro Thr Ser Pro Thr Ala Thr Asn Ile Ser Ser Lys
1               5                   10

<210> SEQ ID NO 59
<211> LENGTH: 14
<212> TYPE: PRT
<213> ORGANISM: Artificial
<220> FEATURE:
<223> OTHER INFORMATION: Tyrosine-protein kinase ABL2;

<400> SEQUENCE: 59

Leu Met Thr Gly Asp Thr Tyr Thr Ala His Ala Gly Ala Lys
1               5                   10

<210> SEQ ID NO 60
<211> LENGTH: 9
<212> TYPE: PRT
<213> ORGANISM: Artificial
<220> FEATURE:
<223> OTHER INFORMATION: Protein phosphatase 1 regulatory subunit 11

<400> SEQUENCE: 60

Cys Cys Cys Ile Tyr Glu Lys Pro Arg
1               5

<210> SEQ ID NO 61
<211> LENGTH: 13
<212> TYPE: PRT
<213> ORGANISM: Artificial
<220> FEATURE:
<223> OTHER INFORMATION: Sphingosine-1-phosphate phosphatase 1;

<400> SEQUENCE: 61

Arg Asn Ser Leu Thr Gly Glu Glu Gly Glu Leu Val Lys
1               5                   10

<210> SEQ ID NO 62
<211> LENGTH: 12
<212> TYPE: PRT
<213> ORGANISM: Artificial
<220> FEATURE:
<223> OTHER INFORMATION: protein tyrosine phosphatase, non-receptor type
      14

<400> SEQUENCE: 62

Tyr Val Ser Gly Ser Ser Pro Asp Leu Val Thr Arg
1               5                   10

<210> SEQ ID NO 63
<211> LENGTH: 26
```

```
<212> TYPE: PRT
<213> ORGANISM: Artificial
<220> FEATURE:
<223> OTHER INFORMATION: Similar to protein phosphatase 1, regulatory
      (Inhibitor) subunit 2;

<400> SEQUENCE: 63

Thr Ser Ala Ala Ser Pro Pro Val Val Pro Ser Ala Glu Gln Pro Arg
1               5                   10                  15

Pro Ile Val Glu Glu Glu Leu Ser Lys Lys
            20                  25

<210> SEQ ID NO 64
<211> LENGTH: 18
<212> TYPE: PRT
<213> ORGANISM: Artificial
<220> FEATURE:
<223> OTHER INFORMATION: dual specificity phosphatase 6

<400> SEQUENCE: 64

Ser Asn Ile Ser Pro Asn Phe Asn Phe Met Gly Gln Leu Leu Asp Phe
1               5                   10                  15

Glu Arg

<210> SEQ ID NO 65
<211> LENGTH: 13
<212> TYPE: PRT
<213> ORGANISM: Artificial
<220> FEATURE:
<223> OTHER INFORMATION: Protein phosphatase 2A B56 delta subunit

<400> SEQUENCE: 65

Arg Lys Ser Glu Leu Pro Gln Asp Val Tyr Thr Ile Lys
1               5                   10

<210> SEQ ID NO 66
<211> LENGTH: 21
<212> TYPE: PRT
<213> ORGANISM: Artificial
<220> FEATURE:
<223> OTHER INFORMATION: protein phosphatase 1, regulatory (inhibitor)
      subunit 2

<400> SEQUENCE: 66

Trp Asp Glu Met Asn Ile Leu Ala Thr Tyr His Pro Ala Asp Lys Asp
1               5                   10                  15

Tyr Gly Leu Met Lys
            20

<210> SEQ ID NO 67
<211> LENGTH: 15
<212> TYPE: PRT
<213> ORGANISM: Artificial
<220> FEATURE:
<223> OTHER INFORMATION: Forkhead box protein K1

<400> SEQUENCE: 67

Ser Ala Pro Ala Ser Pro Thr His Pro Gly Leu Met Ser Pro Arg
1               5                   10                  15

<210> SEQ ID NO 68
<211> LENGTH: 18
<212> TYPE: PRT
<213> ORGANISM: Artificial
<220> FEATURE:
<223> OTHER INFORMATION: Isoform 1 of HMG box transcription factor BBX;
```

```
<400> SEQUENCE: 68

Thr Ala Asp Gly Arg Val Ser Pro Ala Gly Gly Thr Leu Asp Asp Lys
1               5                   10                  15

Pro Lys

<210> SEQ ID NO 69
<211> LENGTH: 31
<212> TYPE: PRT
<213> ORGANISM: Artificial
<220> FEATURE:
<223> OTHER INFORMATION: Transcription factor AP-1

<400> SEQUENCE: 69

Leu Gln Ala Leu Lys Glu Glu Pro Gln Thr Val Pro Glu Met Pro Gly
1               5                   10                  15

Glu Thr Pro Pro Leu Ser Pro Ile Asp Met Glu Ser Gln Glu Arg
            20                  25                  30

<210> SEQ ID NO 70
<211> LENGTH: 31
<212> TYPE: PRT
<213> ORGANISM: Artificial
<220> FEATURE:
<223> OTHER INFORMATION: Isoform 1 of Transcription intermediary factor
      1- beta

<400> SEQUENCE: 70

Leu Gln Ala Leu Lys Glu Glu Pro Gln Thr Val Pro Glu Met Pro Gly
1               5                   10                  15

Glu Thr Pro Pro Leu Ser Pro Ile Asp Met Glu Ser Gln Glu Arg
            20                  25                  30

<210> SEQ ID NO 71
<211> LENGTH: 19
<212> TYPE: PRT
<213> ORGANISM: Artificial
<220> FEATURE:
<223> OTHER INFORMATION: Isoform 1 of Transcriptional repressor p66 beta

<400> SEQUENCE: 71

Leu Thr Pro Ser Pro Asp Ile Ile Val Leu Ser Asp Asn Glu Ala Ser
1               5                   10                  15

Ser Pro Arg

<210> SEQ ID NO 72
<211> LENGTH: 28
<212> TYPE: PRT
<213> ORGANISM: Artificial
<220> FEATURE:
<223> OTHER INFORMATION: Activating transcription factor 7 interacting
      protein;

<400> SEQUENCE: 72

Arg Gln Glu Ser Pro Pro Asn Pro Pro Ile Ser Pro Gly Lys Pro Ala
1               5                   10                  15

Asn Asp Thr Asn Ser Asn Asn Asn Met Thr Tyr Arg
            20                  25

<210> SEQ ID NO 73
<211> LENGTH: 22
<212> TYPE: PRT
<213> ORGANISM: Artificial
<220> FEATURE:
```

-continued

```
<223> OTHER INFORMATION: Isoform Stat3B of Signal transducer and
      activator of transcription 3

<400> SEQUENCE: 73

Tyr Cys Arg Pro Glu Ser Gln Glu His Pro Glu Ala Asp Pro Gly Ser
1               5                   10                  15

Ala Ala Pro Tyr Leu Lys
            20

<210> SEQ ID NO 74
<211> LENGTH: 19
<212> TYPE: PRT
<213> ORGANISM: Artificial
<220> FEATURE:
<223> OTHER INFORMATION: Isoform Stat3B of Signal transducer and
      activator of transcription 3Isoform ALF1B of Transcription factor
      12;

<400> SEQUENCE: 74

Ala Gly Gly Gln Ala Pro Ser Ser Pro Ser Tyr Glu Asn Ser Leu His
1               5                   10                  15

Ser Leu Lys

<210> SEQ ID NO 75
<211> LENGTH: 10
<212> TYPE: PRT
<213> ORGANISM: Artificial
<220> FEATURE:
<223> OTHER INFORMATION: Isoform 3 of Bcl-2-associated transcription
      factor 1;

<400> SEQUENCE: 75

Arg Ile Asp Ile Ser Pro Ser Ala Leu Arg
1               5                   10

<210> SEQ ID NO 76
<211> LENGTH: 15
<212> TYPE: PRT
<213> ORGANISM: Artificial
<220> FEATURE:
<223> OTHER INFORMATION: Isoform 1 of Cyclic AMP-dependent transcription
      factor ATF-2;

<400> SEQUENCE: 76

Lys Met Pro Leu Asp Leu Ser Pro Leu Ala Thr Pro Ile Ile Arg
1               5                   10                  15

<210> SEQ ID NO 77
<211> LENGTH: 18
<212> TYPE: PRT
<213> ORGANISM: Artificial
<220> FEATURE:
<223> OTHER INFORMATION: modulator of estrogen induced transcription
      isoform a

<400> SEQUENCE: 77

Ala Gly Ala Gly Met Ile Thr Gln His Ser Ser Thr Ala Ser Pro Val
1               5                   10                  15

Asn Arg

<210> SEQ ID NO 78
<211> LENGTH: 16
<212> TYPE: PRT
<213> ORGANISM: Artificial
<220> FEATURE:
<223> OTHER INFORMATION: modulator of estrogen induced transcription
```

```
            isoform a

<400> SEQUENCE: 78

Ile Ser Ser Lys Ser Pro Gly His Met Val Ile Leu Asn Gln Thr Lys
1               5                   10                  15

<210> SEQ ID NO 79
<211> LENGTH: 14
<212> TYPE: PRT
<213> ORGANISM: Artificial
<220> FEATURE:
<223> OTHER INFORMATION: Isoform 1 of Cyclic AMP-dependent transcription
      factor ATF-2;

<400> SEQUENCE: 79

Met Pro Leu Asp Leu Ser Pro Leu Ala Thr Pro Ile Ile Arg
1               5                   10

<210> SEQ ID NO 80
<211> LENGTH: 21
<212> TYPE: PRT
<213> ORGANISM: Artificial
<220> FEATURE:
<223> OTHER INFORMATION: Isoform ALF1A of Transcription factor 12;

<400> SEQUENCE: 80

Ala Gly Gly Gln Ala Pro Ser Ser Pro Ser Tyr Glu Asn Ser Leu His
1               5                   10                  15

Ser Leu Gln Ser Arg
            20

<210> SEQ ID NO 81
<211> LENGTH: 18
<212> TYPE: PRT
<213> ORGANISM: Artificial
<220> FEATURE:
<223> OTHER INFORMATION: modulator of estrogen induced transcription
      isoform a;

<400> SEQUENCE: 81

Ala Gly Ala Gly Met Ile Thr Gln His Ser Ser Thr Ala Ser Pro Val
1               5                   10                  15

Asn Arg

<210> SEQ ID NO 82
<211> LENGTH: 23
<212> TYPE: PRT
<213> ORGANISM: Artificial
<220> FEATURE:
<223> OTHER INFORMATION: Transcriptional repressor p66 alpha;

<400> SEQUENCE: 82

Glu Ala Thr Ala Gln Lys Pro Thr Ala Ser Ser Gly Ser Thr Val Thr
1               5                   10                  15

Thr Pro Pro Pro Leu Val Arg
            20

<210> SEQ ID NO 83
<211> LENGTH: 24
<212> TYPE: PRT
<213> ORGANISM: Artificial
<220> FEATURE:
<223> OTHER INFORMATION: Isoform 1 of Eukaryotic translation initiation
      factor 4 gamma 1;

<400> SEQUENCE: 83
```

```
Ile Thr Lys Pro Gly Ser Ile Asp Ser Asn Asn Gln Leu Phe Ala Pro
1               5                   10                  15

Gly Gly Arg Leu Ser Trp Gly Lys
            20

<210> SEQ ID NO 84
<211> LENGTH: 32
<212> TYPE: PRT
<213> ORGANISM: Artificial
<220> FEATURE:
<223> OTHER INFORMATION: Eukaryotic translation initiation factor 4E-
      binding protein 1;

<400> SEQUENCE: 84

Arg Val Ala Leu Gly Asp Gly Val Gln Leu Pro Pro Gly Asp Tyr Ser
1               5                   10                  15

Thr Thr Pro Gly Gly Thr Leu Phe Ser Thr Thr Pro Gly Gly Thr Arg
            20                  25                  30

<210> SEQ ID NO 85
<211> LENGTH: 17
<212> TYPE: PRT
<213> ORGANISM: Artificial
<220> FEATURE:
<223> OTHER INFORMATION: Eukaryotic translation initiation factor 4B;

<400> SEQUENCE: 85

Ser Gln Ser Ser Asp Thr Glu Gln Pro Ser Pro Thr Ser Gly Gly Gly
1               5                   10                  15

Lys

<210> SEQ ID NO 86
<211> LENGTH: 17
<212> TYPE: PRT
<213> ORGANISM: Artificial
<220> FEATURE:
<223> OTHER INFORMATION: eukaryotic translation initiation factor 5B;

<400> SEQUENCE: 86

Ser Val Pro Thr Val Asp Ser Gly Asn Glu Asp Asp Ser Ser Phe
1               5                   10                  15

Lys

<210> SEQ ID NO 87
<211> LENGTH: 24
<212> TYPE: PRT
<213> ORGANISM: Artificial
<220> FEATURE:
<223> OTHER INFORMATION: eukaryotic translation initiation factor 5B;

<400> SEQUENCE: 87

Thr Ala Arg Pro Asn Ser Glu Ala Pro Leu Ser Gly Ser Glu Asp Ala
1               5                   10                  15

Asp Asp Ser Asn Lys Leu Ser Lys
            20

<210> SEQ ID NO 88
<211> LENGTH: 21
<212> TYPE: PRT
<213> ORGANISM: Artificial
<220> FEATURE:
<223> OTHER INFORMATION: Isoform 2 of Epidermal growth factor receptor
      substrate 15-like 1;
```

-continued

```
<400> SEQUENCE: 88

Thr Val Phe Ala Gly Ala Val Pro Val Leu Pro Ala Ser Pro Pro Pro
1               5                   10                  15

Lys Asp Ser Leu Arg
            20

<210> SEQ ID NO 89
<211> LENGTH: 32
<212> TYPE: PRT
<213> ORGANISM: Artificial
<220> FEATURE:
<223> OTHER INFORMATION: Isoform 2 of Epidermal growth factor receptor
      substrate 15-like 1;

<400> SEQUENCE: 89

Ser Leu Glu Gln Tyr Asp Gln Val Pro Asp Gly Val Ser Gly Thr Ser
1               5                   10                  15

Leu Pro Asp Leu Ala Thr Leu Asn Glu Gly Ile Leu Leu Ala Glu Arg
            20                  25                  30

<210> SEQ ID NO 90
<211> LENGTH: 22
<212> TYPE: PRT
<213> ORGANISM: Artificial
<220> FEATURE:
<223> OTHER INFORMATION: Isoform 1 of Rho guanine nucleotide exchange
      factor 10;

<400> SEQUENCE: 90

Asn Asp Leu Ser Ser Ser Ser Gly Ser Leu Asn Leu Ser His Gly Ser
1               5                   10                  15

Ser Ser Leu Glu His Arg
            20

<210> SEQ ID NO 91
<211> LENGTH: 30
<212> TYPE: PRT
<213> ORGANISM: Artificial
<220> FEATURE:
<223> OTHER INFORMATION: Rho guanine nucleotide exchange factor (GEF) 17
      isoform 1;

<400> SEQUENCE: 91

Asp Ser Pro Ser Ala Gly Ser Pro Met Glu Gln Ser Glu Ser Thr Leu
1               5                   10                  15

Ser Gln Ser Pro Thr Ser Pro Thr Thr Arg Pro Thr Leu Lys
            20                  25                  30

<210> SEQ ID NO 92
<211> LENGTH: 25
<212> TYPE: PRT
<213> ORGANISM: Artificial
<220> FEATURE:
<223> OTHER INFORMATION: Death-associated protein 1;

<400> SEQUENCE: 92

Asp Lys Asp Asp Gln Glu Trp Glu Ser Thr Ser Pro Pro Lys Pro Thr
1               5                   10                  15

Val Phe Ile Ser Gly Val Ile Ala Arg
            20                  25

<210> SEQ ID NO 93
<211> LENGTH: 14
<212> TYPE: PRT
```

```
<213> ORGANISM: Artificial
<220> FEATURE:
<223> OTHER INFORMATION: Isoform 1 of Rho/Rac guanine nucleotide
      exchange factor 2;

<400> SEQUENCE: 93

Glu Arg Pro Thr Ser Ala Ile Tyr Pro Ser Asp Ser Phe Arg
1               5                   10

<210> SEQ ID NO 94
<211> LENGTH: 11
<212> TYPE: PRT
<213> ORGANISM: Artificial
<220> FEATURE:
<223> OTHER INFORMATION: Bcl2 antagonist of cell death;

<400> SEQUENCE: 94

Arg Met Ser Asp Glu Phe Glu Gly Ser Phe Lys
1               5                   10
```